United States Patent [19]

Staples et al.

[11] Patent Number: 4,882,137
[45] Date of Patent: Nov. 21, 1989

[54] COATED VETERINARY IMPLANTS

[75] Inventors: Linton D. Staples, East Kew; Robert I. Norman, Dandenong; Robert B. Davey, East Doncaster; Catherine Hastings, Hawthorn; Jennifer Kidd, Camberwell; Jatni Rachmat, South Yarra, all of Australia

[73] Assignee: Gene Link Australia Limited, South Melbourne, Australia

[21] Appl. No.: 52,535

[22] Filed: May 20, 1987

[30] Foreign Application Priority Data

May 23, 1986 [AU] Australia .............................. PH 6077
Mar. 2, 1987 [AU] Australia .............................. PH 604

[51] Int. Cl.[4] ................................................ A61K 2/00
[52] U.S. Cl. .................................... 424/423; 424/424; 424/433; 424/435; 424/482
[58] Field of Search ............... 424/435, 433, 423, 482, 424/424

[56] References Cited

U.S. PATENT DOCUMENTS

| | | | |
|---|---|---|---|
| 3,428,729 | 2/1969 | Anderson et al. | 424/19 |
| 3,991,750 | 11/1976 | Vickery | 128/260 |
| 4,087,444 | 5/1978 | Flaugh et al. | 548/504 X |
| 4,163,011 | 7/1979 | Orts | 260/112.5 |
| 4,252,803 | 2/1981 | Webb | 424/248.5 |
| 4,322,398 | 3/1972 | Reiner et al. | 424/19 |
| 4,346,709 | 8/1982 | Schmitt | 128/260 |
| 4,388,324 | 6/1983 | Horrobin | 514/474 |
| 4,576,604 | 3/1983 | Guittard et al. | 604/890 |
| 4,654,361 | 3/1987 | Samples et al. | 514/419 |
| 4,665,086 | 5/1987 | Short et al. | 514/416 |
| 4,687,763 | 8/1987 | Wurtman | 514/415 X |
| 4,738,679 | 4/1988 | Seamark et al. | 604/892.1 |

FOREIGN PATENT DOCUMENTS

78305/81 6/1982 Australia .
51657/79 7/1983 Australia .
2271832 2/1975 France .

OTHER PUBLICATIONS

Kennaway et al., *Endocrinology*, 110 (6), 2186–2188 (1982).
R. F. Seamark et al., PCT/AU85/00013 (corresponding to U.S. Serial No. 783,954, filed Sept. 26, 1985).

*Primary Examiner*—Thurman K. Page
*Attorney, Agent, or Firm*—Merchant, Gould, Smith, Edell, Welter & Schmidt

[57] ABSTRACT

This invention relates to a method of regulating the reproductive functions of animals, particularly domesticated ruminants, and to veterinary implants for use in such a method.

22 Claims, 14 Drawing Sheets (a)

(b)

COATED VETERINARY IMPLANTS

In our earlier Australian Patent Application No. 78305/81 there is described a method of artificially mimicking changing photoperiod, thereby changing the breeding activity of sheep, goats, deer and other seasonally breeding animals, by the judicious feeding of Melatonin or similarly effective related chemicals.

The role of seasonal environmental factors, in particular the photoperiod, in determining the breeding period of sheep is well established. Under natural conditions the shortening of day length as summer leads to autumn is the main trigger to the reproductive system to commence ovarian cyclicity. Our previous application shows that melatonin treatment can mimick the effects of short day length on ewes, such that the breeding season is advanced and basal prolactin levels are depressed.

In the earlier Patent specification this was achieved by feeding the animal with food containing melatonin or related indole or indole derivatives for a period of time sufficient for the animal to commence cyclic ovarian activity. This was achieved by absorbing the melatonin into food pellets, and in this way 2 mg of melatonin per day was fed to each animal.

In our subsequent Australian Patent Application No. 38111/.85, some of the difficulties related to this prior art were addressed. In particular, the method of administration of the melatonin was changed: rather than administering the agent by the oral route, a subcutaneous implant was used. Such an implant was thought to allow a generally continuous rate of release of the active ingredient sufficient to maintain the blood level of melatonin at or above the natural night-time level for as long as several weeks. However we have now established that the regimen of implants which had to be administered actually gave a saw-tooth profile. Each individual implant actually released measurable Melatonin for only 10–14 days. The major problems with the uncoated implants were:

since individual implants did not release Melatonin for long enough, several consecutive treatments were needed;
the individual profiles were not uniform, and initial dumping was severe.

Moreover, whilst such a formulation of active material has proved to be useful, the relatively short period of maintenance of appropriate blood level of melatonin means that the implant must be replaced at relatively frequent intervals. A further, related difficulty has also been observed. Specifically, during an initial "dumping phase" beginning approximately one hour after implantation, melatonin plasma levels were observed to reach 100–1000 fold normal night-time levels, with possible harmful effects.

It is accordingly an object of the present invention to overcome, or at least alleviate, one or more of the difficulties related to the prior art.

Figure 1:
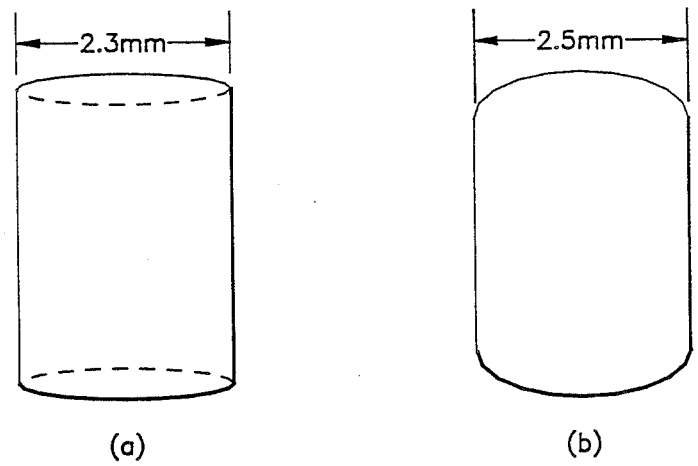
FIGS. 1a, 1b, 2a, 2b, 3, 4, 5, 6, 7, 8, 9, 10, 11, 12, 13, 14, 15, 16, 17 and 18 represent embodiments within the scope of the invention.

Accordingly, in a first aspect, there is provided a coated veterinary implant including (a) a veterinary implant including an effective amount of
  (i) an active ingredient selected from melatonin or related chemicals of the indole class, as hereinafter defined, or mixtures thereof, and
  (ii) a veterinarily acceptable carrier or excipient, and
(b) a coating for said veterinary implant (a) formed from a physiologically compatible polymeric coating composition;

which implant, in use, releases the active ingredient at a rate sufficient to maintain the blood level of melatonin or related chemicals of the indole class at or above a level sufficient, and for a period sufficient to regulate seasonal breeding activity and/or seasonal physiological responses of an animal to be treated.

A blood level sufficient may in certain animals such as domesticated ruminants be at or above the natural night time level of melatonin. The level sufficient may be at or above the natural daytime blood levels of melatonin in other animals.

By "seasonal physiological responses" as used herein in the description and claims we mean changes in the physiology of the animal to be treated which are affected by season and include pelage, development of horn or antler, appetite and the like. By the term "blood level of melatonin or related chemicals" as used herein in the description and claims we mean the amount of such chemicals detectable in a blood sample during daylight hours from a vein at other than a vein which is directly draining the implant site.

For domesticated ruminants, such as sheep and goats, a sufficient level is approximately 1.0 picomoles per milliliter (1000 pM).

It will be understood that the coated veterinary implant according to this aspect of the present invention provides a substantial improvement over the prior art as the desired rate of release may be maintained for at least 3 weeks, more preferably for approximately 30–50 days.

A typical profile for daylight plasma melatonin levels in sheep following coated veterinary implant treatment shows three delivery phases as follows:

Phase 1—"Dumping Phase"

This commences within one hour following implantation and has a duration of approximately 4 hrs. During this period there is initial "dumping" of melatonin so that plasma levels rise rapidly to maximum levels which do not excede 10 fold normal physiological levels. (This contrasts with early studies in which prototype uncoated implants or depot injections gave dumping in excess of 100–1000 fold normal night-time levels).

Phase 2—"Plateau Plase"

This phase commences within one day after implantation and lasts for approximately 37 days. During this period, daylight plasma melatonin levels are maintained continuously at about 1–5 fold normal night-time values. Mean ($\pm$SEM) daylight plasma concentrations during the plateau phase for the normal coated implant are $2597 \pm 279$ pico molar (pM).

It should be noted that variability between bleeds in plasma levels is associated with a marked (5 fold) difference in plasma melatonin concentration in the jugular venous effluent ipsilateral and contralateral to the side of implantation. More recent profiles in which plasma is always collected contralaterally to the side of implantation show a more uniform plateau phase.

Phase 3—"Declining Phase"

This phase commences after approximately 37 days from implantation and has a duration of less than 10 days. During this phase daylight plasma melatonin levels decline rapidly to return to the normal daylight range (typically undetectable). This phase is thought to reflect exhaustion of the active ingredient, melatonin, from the controlled delivery implant. Plasma samples taken during daylight over extended periods following exhaustion of similar implants show no detectable Melatonin concentration.

The active ingredient of the coated veterinary implant according to this aspect of the present invention may be selected from Melatonin or related or derived chemicals of the indole class. While the present invention describes the use of Melatonin per se, it has been established in the prior art that certain other related or derived molecules may exert a similar biological effect. Thus Kennaway et al. (1986) have demonstrated that certain classes of Melatonin derivative or analogue (notably those halogenated at the indol-6 position, those carrying a saturated bond at the indol-2,3 position, and those arising from cleavage of the indolyl ring) have a similar, although lesser, effect on serum prolactin levels when administered to sheep, compared to Melatonin. (Kennaway, D. J., P. Royles, E. A. Dunstan and H. M. Hugel, 1986. Prolactin Response in Border Leicester×Merino Ewes to Administration of Melatonin, Melatonin Analogues, a Melatonin Metabolite and 6-Methoxybenzoxazolinone. Australian Journal of Biological Sciences, 39:427–433). Similarly, Frohn et al (1980) using a biological assay highly specific for Melatonin-like activity, have established the biological activity of a variety of analogues, derivatives, and related indole compounds, relative to Melatonin itself. (Frohn, M. A., C. J. Seaborn, D. W. Johnson, G. Phillipou, R. F. Seamark and C. D. Matthews, 1980. Structure-activity Relationship of Melatonin Analogues. Life Sciences, 27:2043-2046). Accordingly, the active ingredient of the coated veterinary implant according to this aspect of the present invention may be selected from MELATONIN (N-acetyl 5-methoxy tryptamine)
MELATONIN analogues substituted at the amino nitrogen, e.g.:
N-propionyl/N-butyryl
MELATONIN analogues substituted at the 5- position, e.g.: 5-ethoxy (i.e. N-acetyl O-ethyl serotonin)
5-propoxy (i.e. N-acetyl O-propyl serotonin)
MELATONIN analogues substituted at the 6- position,
  e.g. Halo-substituted: 6-fluoro/6-bromo/6-chloro/6-iodo
Hydroxy- substituted
Suphatoxy- substituted
Alkyl- substituted: 6-methyl/6-ethyl/6-isopropyl etc.
Alkoxy- substituted, e.g. 6-methoxy
Silylated, e.g. 6-(t-butyl)dimethylsiloxy
SATURATED MELATONIN DERIVATIVES, such as (2,3-dihydro)melatonin and 6-chloro-(2,3-dihydro)melatonin (together with all the 5-, 6- and N- substituted saturated derivatives thereof as described above)
RING-CLEAVED MELATONIN derivatives (including all the 5- 6- and N- substituted derivatives thereof as described above, and similarly, saturated derivatives thereof), such as
N-acetyl 5-hydroxy kynurenamine
N-acetyl 5-methoxy kynurenamine
RELATED INDOL (SEROTONIN) derivatives, such as
N-acetyl serotonin
N,O-iacetyl serotonin
N-acetyl tryptamine
Serotonin
5-methoxyl tryptophol
5-methoxy tryptamine
OTHER DERIVATIVES and RELATIVES of MELATONIN, such as
  N-alkyl and/or N,N-dialkyl analogues of tryptamine, serotonin and melatonin
  N-aryl and/or N,N-diaryl analogues of tryptamine, serotonin and melatonin
Similarly, mixed N-alkyl, N-aryl derivatives 5-substituted derivatives of tryptamine, Ureido- analogues of tryptamine and serotonin; or mixtures thereof.

The active ingredient may be present in an amount of from approximately 25 to 98% by weight based on the total weight of the coated implant, depending on the species and breed to be treated. For animals such as sheep, deer and the like the active ingredient may be present in amounts of from approximately 75 to 98% by weight based on the total weight of the coated implant.

For animals such as mink and fox amounts of active ingredient of from approximately 25 to 75% by weight may be used.

The veterinarily acceptable carrier or excipient may include a compressible pharmaceutical vehicle selected to control the release rate of the active ingredient. The carrier or excipient may be present in amounts of approximately 1 to 75% by weight based on the total weight of the coated implant.

Such a vehicle may be a high molecular weight form of ethyl cellulose. The form of ethyl cellulose may be chosen from the range of ethoxylated cellulose derivatives sold under the trade designation "Ethocel" and available from the Dow Chemical Company. Ethocel Standard and Ethocel Medium, both of viscosity grades between 7 cP and 100 cP, are preferred.

Alternatively, or in addition, the veterinary carrier or excipient may include an acid salt. The acid salt may be a phosphate salt. The vehicle may be an alkaline earth metal salt. A calcium phosphate is preferred. A hydrated acid salt may be used. A dibasic calcium phosphate dihydrate is preferred. The acid salt may be a calcium phosphate of the type sold under the trade designation "Encompress" and available from Edward Mendell Co. Inc., New York, United States of America.

Preferably the veterinary implant (a) according to the present invention is formed by granulation and compression, and may therefore further include an effective amount of
  (iii) a granulating agent, and/or
  (iv) a compression lubricant.

The granulating agent (iii) may be selected from a high molecular weight compound or a cellulose compound or mixtures thereof. The high molecular weight compound or the cellulose compound may be a water-insoluble compound. As the high molecular weight compound, vinyl polymer may be used.

Polyvinylpyrrolidone (PVP) is preferred. The PVP utilised in the implants according to this aspect of the present invention may be selected from the range of vinyl pyrrolidone polymers manufactured and supplied by the GAF Corporation of the United States of America under the trade designation "Plasdone", including Plasdone K-29/32 and Plasdone K-90. Plasdone K-

29/32 has a volume average molecular weight of approximately 38,000 while the K-90 form has a volume average molecular weight of approximately 630,000.

The molecular weight of the polymer affects the following properties of the material.
(1) Viscosity in solution
(2) Adhesive Properties
(3) Rate of solution (dissolution)
(4) Rate of absorption and excretion.

As the K-value of Plasdone excipient increases, values for the first two properties listed above increase while the last two decrease.

The cellulose compound may be selected from ethyl cellulose, methyl cellulose, and cellulose esters such as cellulose acetate, cellulose acetate phthalate or compounds sold under the trade designation "Methocel" and "Ethocel" and available from Dow Chemical Company. Alternatively, or in addition, naturally occurring, water-insoluble high molecular weight compounds such as the waxes, for example, beeswax, may be included.

Regardless of which granulating agent (iii) is chosen, that agent may be present in amounts of from approximately 1% to 10% by weight, preferably 1 to 5% by weight based on the total weight of the veterinary implant.

The compression lubricant (iv) may be present in an amount of approximately 0.1 to 5% by weight, preferably 0.5 to 2.0% by weight, based on the total weight of the coated veterinary implant. The compression lubricant additionally may function as a tabletting binder. The lubricant may be a food grade lubricant. The lubricant may be a food source lubricant. The lubricant may be derived from vegetable oil. The lubricant may be a lubricant of the type sold under the trade designation "Lubritab" and available from Edward Mendell Co. Inc., New York, United States of America.

The physiologically degradable polymeric coating composition of the veterinary implant coating (b) may include a film-forming high molecular weight polymer. The film-forming high molecular weight polymer may be water-insoluble. Such a polymer may be a form of ethyl cellulose. The form of ethyl cellulose may be chosen from the range of ethoxylated cellulose derivatives sold under the trade designation "Ethocel" and available from the Dow Chemical Company. Ethocel Standard and Ethocel Medium, both of viscosity grades between 7 cP and 100 cP, are preferred. The polymer may be provided in the form of an emulsion, dispersion or solution.

The film-forming high molecular weight polymer may be a form of acrylic polymer. The form of acrylic polymer may be selected from a group of polymers and co-polymers synthesised from acrylic and methacrylic acid, esters thereof and mixtures thereof. The acrylic polymer may be selected to form a water-insoluble film whose permeability is independent of PH. The acrylic polymer may be chosen from the range of coating materials sold under the trade designation "Eudragit" and available from Rohm Pharma GmbH, of Darmstadt, Federal Republic of Germany. Eudragit RL and Eudragit RS are preferred.

Alternatively an inorganic film-forming high molecular weight polymer coating may be used. A silicon polymer may be used. A silastic-type polymer coating may be used.

The physiologically degradable polymeric coating composition may further include a diluent or solvent for the film-forming high molecular weight polymer. The diluent or solvent for preparation of the physiologically degradable polymeric coating composition may be chosen so as not to dissolve the active ingredient from the implant during manufacture. Accordingly, the diluent or solvent may be an organic solvent, or a mixture of organic solvents. Where esters of cellulose are chosen as the polymer, the preferred diluent or solvent may be dichloromethane. Alternatively, where acrylic resins are chosen as the coating substance, a mixture of acetone and isopropanol may be the preferred diluent or solvent.

In a preferred form of this aspect of the present invention, the physiologically degradable polymeric coating composition may further include an effective amount of a plasticising agent. Concentrations of plasticising agent of between 0.5% and 10% by volume of the final solvent may be used. Concentrations in the range 2% to 6% by volume of the final solvent are preferred. The plasticiser may be an organic ester. The dibutyl ester of phthalic acid is preferred. Alternatively, the plasticiser may be a glycol. Glycerol or polyethylene glycol may be used.

Preferably the coated veterinary implant including
(a) a veterinary implant including
  approximately 2.5 to 100 milligrams more preferably 17.5 to 30 millograms of melatonin,
  0 to approximately 0.2 milligrams of polyvinylpyrrolidone;
  approximately 2.5 to 5 milligrams of ethyl cellulose; and
  approximately 0.2 to 0.3 milligrams of a compression lubricant, and
(b) a first coating for said veterinary implant including approximately 0.01 to 1.0 milligrams of ethyl cellulose polymer.

Preferably the coated veterinary implant further includes
(c) a second coating for said veterinary implant including approximately 0.01 to 1.0 milligrams of ethyl cellulose polymer.

Preferably, the coated veterinary implant is of generally cylindrical shape and having dimensions of approximately 2 to 10 mm, preferably 2 to 5 mm long and 2 to 3 mm preferably 2.5 mm in diameter.

The ends of the implant may be rounded slightly, as illustrated in FIG. 2.

In a further aspect of the present invention there is provided a method for preparing a coated veterinary implant, which method includes providing an effective amount of
(a) an active ingredient selected from melatonin or related chemicals of the indole class, or mixtures thereof;
(b) a veterinarily acceptable carrier or excipient therefor; and
(c) a physiologically compatible polymeric coating composition;
mixing the components (a) and (b) together for a time sufficient to form an intimate mixture thereof;
subjecting the mixture of a granulating step;
compressing the granulated mixture under a pressure and temperature sufficient to form a veterinary implant, and
coating the veterinary implant with the polymeric coating composition,
which implant, in use, releases the active ingredient at a rate sufficient to maintain the blood level of melatonin or related chemicals of the indole class at or above a level sufficient, and for a period sufficient to regulate seasonal breeding activity and/or seasonal physiological responses of an animal to be treated.

Mixing the components at each stage can be performed using any suitable container.

Where the granulation step involves wet granulation, the inclusion of a granulating agent, as described above, is preferred. Sufficient of the selected granulating agent, preferably in an appropriate solvent, may be admixed with the prior dry ingredients to yield a damp mass which is then granulated by passage through a sieve of the desired mesh size and allowed to dry. The granulating agent is preferably selected from ethyl cellulose and polyvinyl pyrrolidone. A volatile solvent such as ethanol may be used as the solvent or the granulating agent. The granulation process can be performed more than once if desired. Granulation may also be achieved both in mechanical devices and by extrusion methods.

The mixture is then subjected to a compression step. The compression may be conducted under pressures of up to several hundred bar, for example 500 to 1200 bar. Preferably compression is undertaken with pressures of approximately 100 to 800 bar. The veterinary implant may be compressed into any suitable form. For example, the veterinary implant may be in the form of a tablet, a bead, a cylinder, a rod or a plate. A cylindrical pellet form is preferred. In this form, a standard single-punch tableting press may be used. A compression lubricant may be included at this stage. The preferred compression lubricant is "Lubritab".

In a preferred form the physiologically compatible polymeric coating composition includes a first coating solution including approximately 0.5 to 2.5% of ethyl cellulose polymer, and a second coating solution including approximately 0.25 to 1.25% of ethyl cellulose polymer and the coating step includes coating the veterinary implant sequentially with said first coating solution and second coating solution. It has been found that an improved consistent release profile may be achieved utilising multiple coatings.

The second coating, in a preferred aspect, may be added in multiple stages. The coated implant may be allowed to dry in full or in part dry each stage. The coated implant may be dusted with talc between each stage if desired.

The implants may be individually or severally loaded into a separate chamber of a plastic cartridge. The plastic cartridges may be placed into a "gun" and the implant delivered subcutaneously through a large bore needle.

Although subcutaneous implantation is our preferred route for administering these implants, they may be effective when administered orally, vaginally, intraperitoneally (I.P.), percutaneously or intramuscularly (I.M.). The IM or I.P routes may be used in particular in fur-bearing animals, such as mink and angora rabbits.

In a further aspect of the present invention there is provided a method of regulating the seasonal breeding activity and/or related physiological responses of animals which method includes inserting into an animal to be treated at a suitable implantation site at least one coated veterinary implant including (a) a veterinary implant including an effective amount of (i) an active ingredient selected from melatonin or related chemicals of the indole class, as hereinafter defined, or mixtures thereof, and (ii) a veterinarily acceptable carrier or excipient, and (b) a coating for said veterinary implant (a) formed from a physiologically compatible polymeric coating composition;

which implant, in use, releases the active ingredient at a rate sufficient to maintain the blood level of melatonin or related chemicals of the indole class at or above a level sufficient, and for a period sufficient to regulate seasonal breeding activity and/or seasonal physiological responses of an animal to be treated.

Administration of 2 or more implants has been found to be advantageous. Administration of 2 or more implants simultaneously may provide a more reliable treatment in some breeds/species. Administration of 2 or more implants sequentially may provide an effect over a still more extended period.

In the following description, reference will be made to the efficacy of the veterinary implants in sheep, deer and mink. It should be understood, however, that such animals are mentioned for illustrative purposes only and the veterinary implant is applicable to animals generally. The veterinary implant may be applied to animals including sheep, goats, horses, deer, pigs, ferrets, mink, fox, sable, ermine, bear, camels, lamas and the like. The veterinary implants may further be applied to the regulation of seasonal breeding activity in birds, reptiles, including alligators, crocodiles, turtles and snakes, and fish including sturgeon, trout, salmon and eels.

The method of regulating the reproductive functions in animals may be such as to advance or delay the onset of oestrus or breeding activity, to induce or delay the onset of ovulation or sperm production, or to increase the rate of ovulation or sperm production. In advancing or delaying the onset of ovulation or sperm production, the duration of the animal's breeding season may be altered. Some or all of these effects may continue for an extensive period, e.g. two to four years, or throughout the reproductive life of the animal.

Preferably the implantation site is a subcutaneous implantation site.

Preferably, the subcutaneous implantation site will be at the base of the ear of the animal to be treated.

The animal to be treated may be a mature animal. The seasonal breeding activity may be modified by accelerating the onset of oestrus or the breeding cycle.

The animal to be treated may be a pre-pubescent animal and the seasonal breeding activity is modified by delaying the onset of puberty and thus the onset of the breeding season is altered over a number of years.

In general, the animal to be treated will be a female. However, alternatively or in addition the male of the species may be treated. This is preferable for deer and goats and to a lesser extent, sheep. Where changes in pelage (fur/wool/coat/pelt production etc.) are sought, both male and female animals may be treated.

In a further preferred aspect of this invention, the reproductive functions of female animals may be regulated by increasing the rate of ovulation in such treated animals.

In a further related aspect, this invention provides a method of regulating the physiological characteristics of animals which method includes inserting a coated veterinary implant of the type described above into an animal to be treated.

With respect to sheep, for example, the induction of an earlier onset to the breeding season has a number of advantages including allowing earlier joining for lamb drop in more favourable weather, longer growth periods for lambs and minimizing potential labour clashs for management of lambing and for marking with that required for cropping.

The coated implant treatment permits a defined joining time since treated ewes reliably respond to "ram effect" and therefore mate and conceive at about 3 to 4 weeks after introduction of rams. Although the implants are typically used in sheep in conjunction with the "ram effect" they will induce changes in reproductive activity without the additional use of rams.

The treatment may shorten the conception period so that lambing period will be condensed (this allows for an even crop of lambs and maximization of labour inputs over a short lambing period).

The treatment induces the normal peak seasonal ovulation rates to occur early in the season. Fecundity (number of lambs/ewe joined) is therefore increased by 14 to 30%. This is due almost entirely to an increased occurrence of twins.

Certain other physical characteristics of animals may be regulated in a similar way by means of the coated sustained-release melatonin implant described herein. The physiological characteristics which may be regulated are those usually associated with reproductive activity or seasonal changes, and include changes in the thickness or the colour of the animal's coat, pelt or fur, and the development of horn or antler.

The present invention will now be more fully described with reference to the accompanying examples. It should be understood, however, that the examples are illustrative only and should not be taken in any way as a restriction on the generality of the invention described above.

EXAMPLE

Example 1 to 5

Veterinary implants according to the present invention were prepared by utilising the ingredients and methods of manufacture as specified below. In each example the ingredients were intimately mixed together and wet granulated utilising a volatile solvent.

The wet granulation step consists of moistening the mixture of active ingredient and, if required, diluting with the granulating liquid comprising the granulating agent in solution in water, alcohol, or mixture of those two, or any other acceptable liquid to moisten and bind the powders together by causing the particles to adhere to each other. The wet mass produced by mixing the liquid with the solid should have a doughlike consistency so that a handful can be formed into shape without crumbling. When pressed into a ball with the hands and broken in half, it should give a clean fracture without sticking or crumbling. If the mass has a tendency to stick or not break clean, the granulation is usually too wet. If the mass crumbles or breaks into pieces it is too dry.

For the purpose of granulating melatonin the granulating agent of choice is PVPK-90, dissolved at a concentration of 5% w/v in 80% aqueous ethanol. To form granules the wet mass was passed through a 12 mesh (1.4 mm) sieve and allowed to dry at room temperature. The dry granules were then passed through a 25 mesh (600 micron) sieve prior to mixing with the lubricant.

Implant cores were then produced by compression of the granulated powder in a standard tabletting press. The implant cores so produced were then coated, either by hand or by means of a standard tablet coating machine, such as the device sold under the trade name "Hi-Coater Mini" and available from the Freund Company Ltd., of Tokyo, Japan.

The coating agent is preferably an Ethocel product of viscosity in the range of 50 to 100 cP, as a 5% w/v solution in dichloromethane. To this solution was added dibutylphthalate at a concentration of 2% w/v, as a plasticiser.

Table 1 describes the specific chemical formulations used in the examples. Examples 1 and 2 release above-threshold levels in animals such as sheep or deer. Example 3 may release levels close to the threshold in larger animals and is more suited to smaller animals. Example 4 is suitable for smaller animals such as mink. The physical dimensions of implants 1 to 4 are essentially similar, and are given in FIG. 1. Implant 5 is correspondingly smaller, in either or both dimensions depending upon the method of manufacture.

TABLE 1

IMPLANT FORMULAE
All weights are in milligrams

| CORE: | FORMULATION EXAMPLE | | | | |
|---|---|---|---|---|---|
| | 1 | 2 | 3 | 4 | 5 |
| Melatonin | 20 | 17.5 | 10 | 5 | 5 |
| P.V.P. K-90 (5% in 80% Ethanol) | 0.2 | 0.2 | 0.2 | 0.2 | 0.1 |
| Ethocel M 100cP | 0 | 2.5 | 10 | 15 | 3 |
| Lubritab | 0.3 | 0.3 | 0.3 | 0.3 | 0.2 |
| COATING: Ethocel M 50cP (from 5% solution in dichloromethane plus 2% dibutyl phthalate as plasticiser) | 0.6 to 1.5 depending on coating method | | | | |

Example 6

Coated Veterinary Implants—Scaled-Up Method of Manufacture

The manufacture of implants is performed in two stages. The first is to produce the implant cores and the second is the coating of the cores to produce the final implant.

Granulation and Production of Implant Cores (to produce 8000 cores)

(1) Weigh 10 g of Ethocel S100 and dissolve in 100 mL of ethanol 95%.
(2) Weigh 200 g of melatonin and crush in a mortar with a pestle.
(3) Weigh 0.2 g of quinoline yellow and mix in gradually with the melatonin.
(4) Transfer the melatonin to a round bottomed vessel.
(5) Add 45 g of the Ethocel solution prepared in step 1 to the melatonin and mix well until a stiff mixture is obtained.
(6) Granuate by forcing the mixture through a sieve (mesh #12) to form granulates.
(7) Spread the granules out on a tray and dry overnight at room temperature.
(8) Crush the granules in a mortar with a pestle.

Transfer to a round bottomed vessel and add a further 45 g of the Ethocel solution prepared in step 1. Mix well.

(9) Repeat steps 6, 7 and 8.

(10) Sieve the granules (mesh #24) and record the weight of the sieved granules.

(11) Calculate the weight of hydrogenated vegetable oil (Lubritab) required (3% of sieved granule weight).

(12) Weigh the Lubritab and 0.2 g of quinoline yellow and mix together in a mortar and pestle. Add to the granules and blend well.

(13) Compress the granules into implant cores to a hardness of approximately 10 kPa using a single punch tableting machine.

Coated Veterinary Implants—Method of Manufacture Coating of the Implant Cores (1) Prepare 150 mL of a solution of Ethocel M50 1.25% and dibutylphthalate 0.5% in dichloromethane. (Coating Solution 1).

(2) Prepare 300 mL of a solution of Ethocel M50 0.625% and dibutylphthalate 0.25% in dichloromethane. (Coating Solution 2).

(3) Load the Hi-Coater pan with 300 g of implant cores and set the pan speed at 5 r.p.m., inlet air temperature 40° C., outlet air 50° C. Maintain these parameters for 10 minutes as a warm up phase.

(4) Increase the pan speed to 30 r.p.m. and spray 150 mL of the Coating Solution 1.

(5) Maintain the pan speed and temperature and spray 100 mL of the Coating Solution 2.

(6) Decrease the pan speed to 5 r.p.m. and cool the implants to room temperature for 10 minutes. Dust the implants with 0.5 g talc.

(7) Increase the pan speed to 30 r.p.m. and inlet air temperature to 40° C., outlet air 30° C. spray 100 mL of the solution prepared in step 2.

(8) Reduce the speed to 4 r.p.m. and cool to room temperature for 10 minutes. Dust the implants with 0.5 g talc.

(9) Repeat steps 7 and 8.

(10) Transfer to a sealed light-proof container for storage.

Coated Veterinary Implants—Formulation

| Coated Veterinary Implants - Formulation | | |
|---|---|---|
| Implant Cores | | |
| Ethylcellulose (Ethocel S100) | 10 g | |
| Ethanol 95% | to 100 mL | |
| Melatonin | 200 g | |
| Hydrogenated Vegetable Oil (Lubritab) | 3% of sieved granule weight | |
| Quinoline Yellow | 0.4 g | |
| Implant Coating | | |
| Coating Solution 1: | | |
| Ethylcellulose (Ethocel M50) | (1.25%) | 1.875 g |
| Dibutylphthalate | (0.5%) | 0.875 mL |
| Dichloromethane | to | 150 mL |
| Coating Solution 2: | | |
| Ethylcellulose (Ethocel M50) | (0.625%) | 1.875 g |
| Dibutylphthalate | (0.25%) | 0.875 mL |
| Dichloromethane | to | 300 mL |
| Implant Cores | | 300 g |
| Purified Talc | | 1.5 g |

FIELD TRIALS

General Experimental Procedure

Trials were conducted on Department of Agriculture and Rural Affairs Research Institutes and on private farms. For farm trials the testing protocol involved pre-visits and discussions with the co-operating farmer. Ewes were individually tagged and weighed then allocated to experimental groups either randomly or where appropriate according to age or weaning period. Trial animals were grazed under normal management conditions for the farm and received normal animal health treatments such as for fly strike (e.g. crutching, jetting) and parasite control (e.g. drenching) throughout the trial period. Treated animals were given no supplementary treatments which would in any way influence the assessment of the implant treatment effect.

Implants were inserted by DARA staff and all rams used underwent health checks including examination of feet and mouth, testicle palpation, blood tests for brucellosis and semen tests (motility and morphology of sperm after electroejaculation).

Ram percentages were normal for breeding flocks, i.e. 2 to 3%. Joining times were selected by the farmer in consultation with DARA staff. Joining times chosen were appropriate for each farmer's requirements but all joinings were early in relation to the peak seasonal reproductive performance for the breed under test.

For farm trials all treatment ewes were usually joined as one group. When separate mating groups were required, such as for "ewe effect" controls on farms or for Institute trials, rams were allocated randomly to experimental groups. All rams were fitted with "Sire Sine" harnesses and crayons. Crayons were changed every fortnight. Ewes were weighed at joining.

Mating flocks were yarded at intervals of 1 to 4 days throughout the joining period and ewes were examined for mating marks. Where possible, cross checks were made of previous mating marks for ewes which mated more than once.

All ewes were weighed at the end of joining and, where appropriate, pregnancy was diagnosed by ultrasonic scanning at mid gestation (approximately 70 days from ram introduction). The number of fetuses present and fetal age was estimated without reference to experimental group. After initial diagnosis, cross reference was made to expected fetal age on the basis of mating records and anomalies (e.g. missed mating marks or breakthrough oestrus in pregnant ewes) were corrected.

Animals from which certain data was not recorded, were excluded from analysis.

All deaths, injuries or abnormalities in the flocks were recorded throughout the experimental period.

Figure 17:
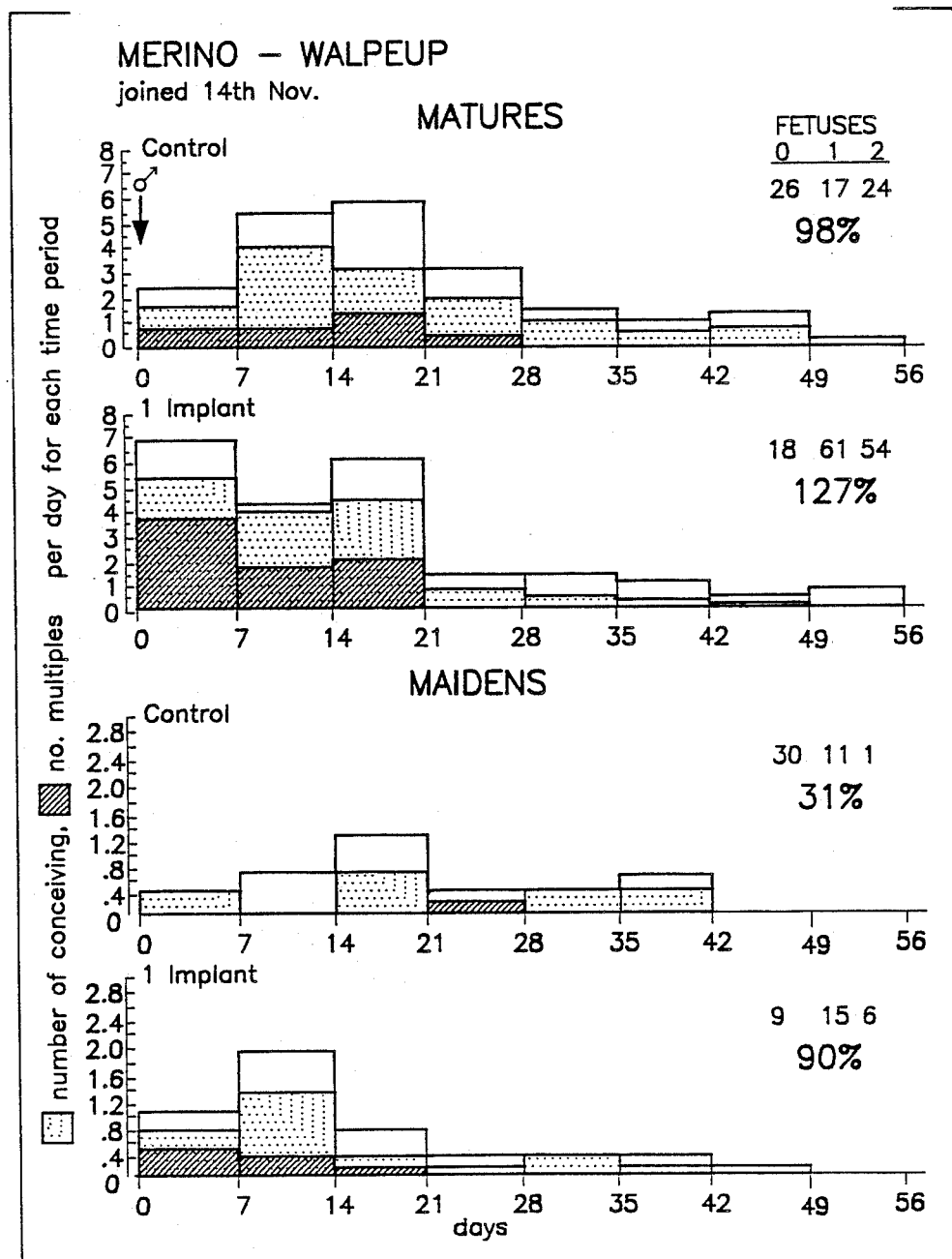

The following examples may be summarised as follows:

| | Blood profiles |
|---|---|
| Example 7: | |
| Field Trial 1 | |
| Example 8: | Changes in ovarian function following use |
| Field Trial 2 | of the implants - supports our claim for increases or decreases in ovulation rate and mating. |
| Example 9: | Use of implants in fertile mating flocks |
| Field Trials 3a - Merino 3b - BLxM 3c - Romney | early in the season - support claims for increased fertility and fecundity, shortened mating and lambing periods, earlier joining and lambing, and optimisation of treatment in relation to introduction of rams. |
| Example 10: | Use at different times of the year |
| Field Trial 4 | - supports claims for usefulness at different times |
| Example 11: | |
| Field Trial 5 | Effects in different age groups |
| FIG. 17 | Mating and conception patterns |
| Table 13 | Four week treatment in Mature and Maiden |

Figure 18:
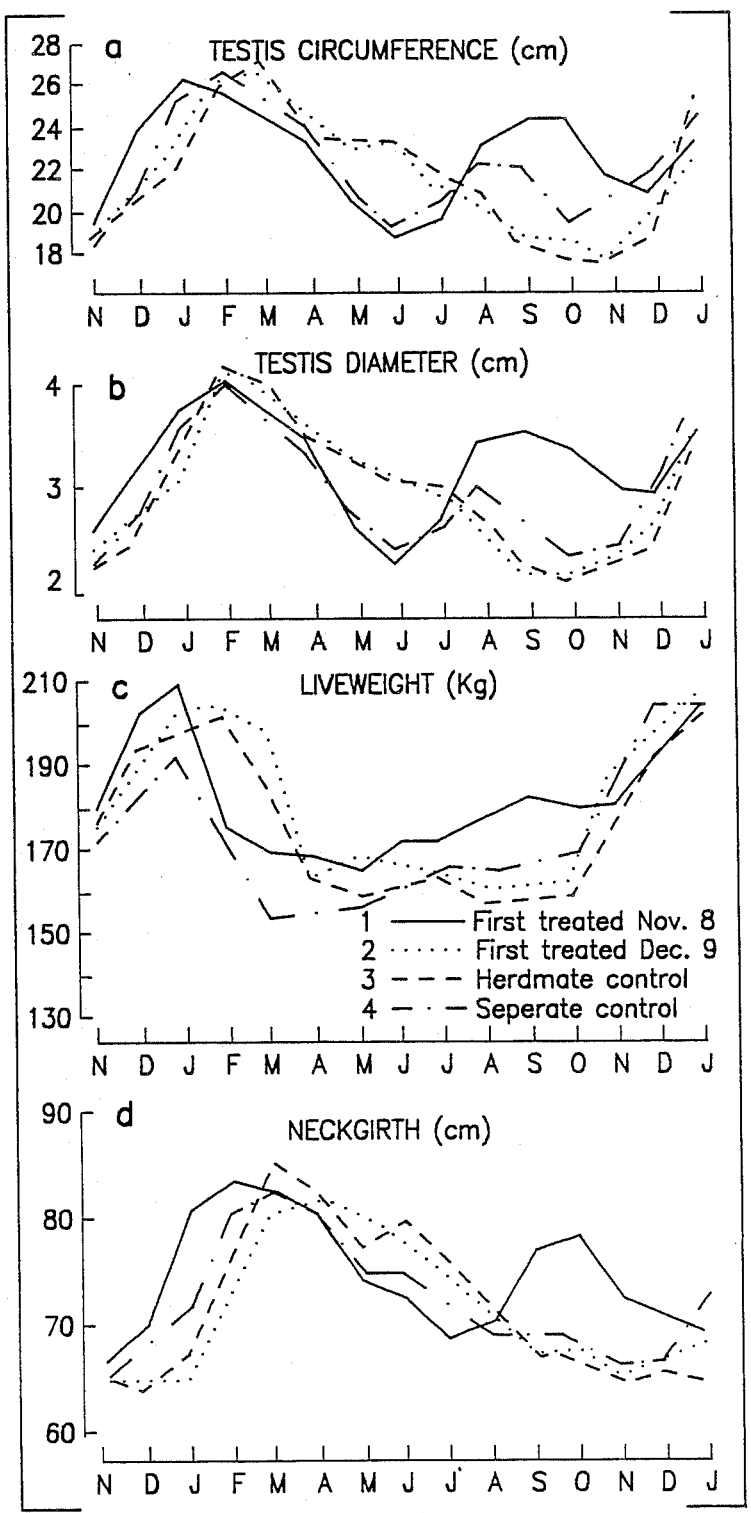

| -continued | |
| --- | --- |
| Blood profiles | |
| Merinos | |
| Example 12: | |
| Field Trial 6 | Effects on extending season |
| Table 14 | Extension of the season - Corriedale |
| Example 13: | |
| Field Trial 7 | Effects in goats |
| Table 15 | Early mating in Angora goats |
| Example 14: | |
| Field Trials 8 & 9 | Effects in deer hinds - pellage and mating |
| Table 16 | Early induction of summer coat - Red hinds |
| Table 17 | Early onset of ovarian activity - Mature Red hinds |
| Table 18 | Early onset of ovarian activity - Maiden Red hinds |
| Example 15: | |
| Field Trial 10 | Effect in deer stags |
| FIG. 18 | |
| Example 16: | |
| Field Trial 11 | Effect on pellage in mink |
| Table 19 | Pellage changes in mink |

Specific conditions for each trial are identified in subsequent sections.

Example 7

Field Trial 1

Figure 2A:
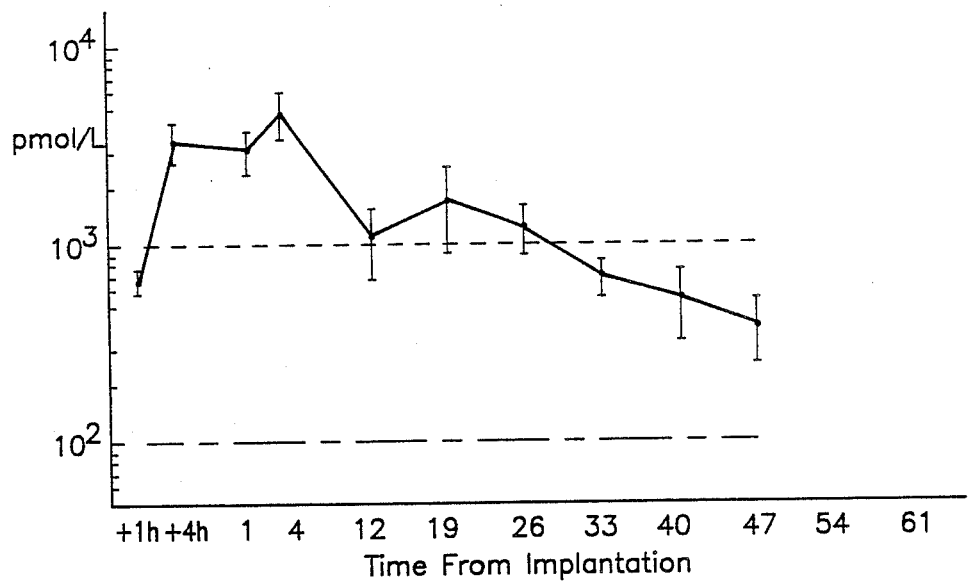
Figure 2B:
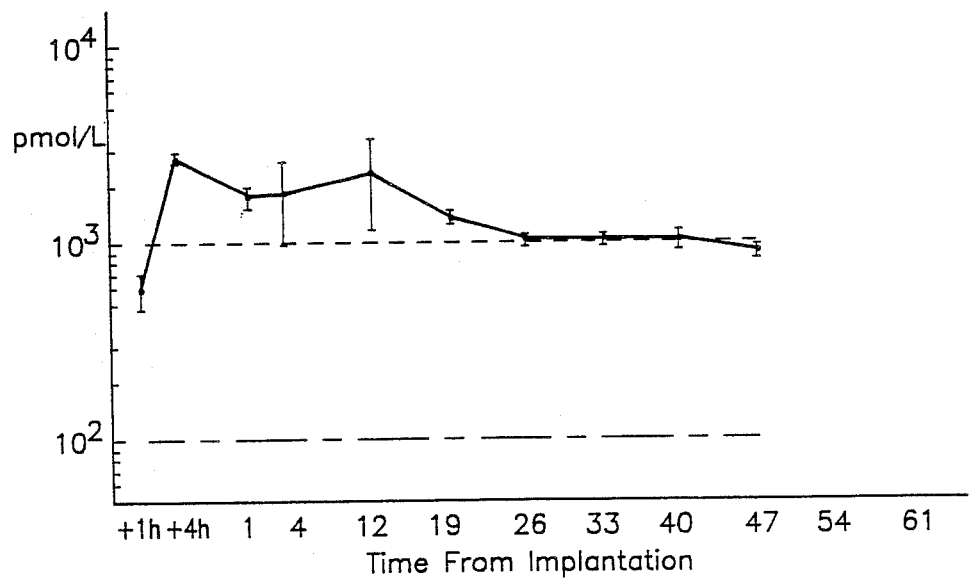
Figure 3:
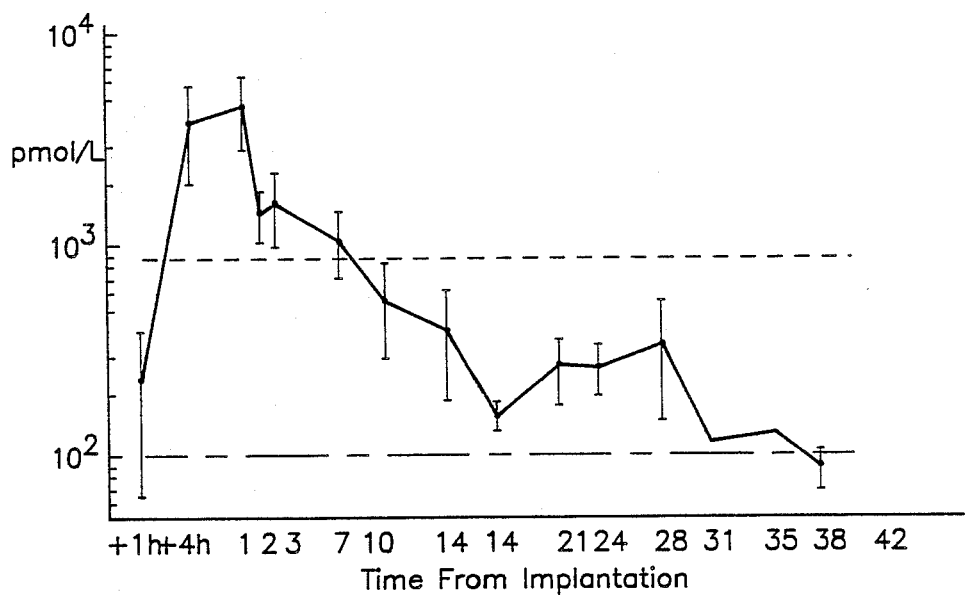

When a single implant such as in Example 2 is implanted subcutaneously at the base of one ear in each of four Merino or Merino-Border Leicester cross-bred ewes, the subsequent average level of melatonin in the animals' serum is shown in FIG. 2a and b, compared with the equivalent level resulting from implantation with uncoated implants. (FIG. 3). The reliability of treatment in some species and breeds may be further improved by administering two implants simultaneously (see FIG. 2b).

Example 8

Field Trial 2

Ovarian response to coated implants

This experiment was designed to define the ovarian response to coated implant treatment. This was necessary in order to provide a firm physiological basis for the development of a practical field treatment in mating flocks.

Conditions specific to this trial

Mature Corriedale ewes (n=100/group) were used for this trial. In this trial two types of coated implant were used. One implant was the normal coated implant which contains 18 mg of melatonin and maintains daylight plasma melatonin levels at $2597\pm279$ pico molar from days 1 to 37 following implantation (i.e. for approximately 5 weeks, see FIG. 3). The second implant was a low dose prototype which contained 10 mg of melatonin and maintained plasma levels at $704\pm150$ pico molar for the same period. For each group, implants were administered on two separate occasions, the second four weeks after the first, so that treatment was maintained continuously for about 9 to 10 weeks. Comparison between treatment groups permitted assessment of the dose-dependence of effects. Control animals received no treatment (previous studies have shown that placebo implants affect neither the melatonin levels or reproductive responses in ewes).

This trial was conducted at the Animal Research Institute Werribee. All treated and control groups were maintained in mutual isolation and vasectomized (teaser) rams were maintained with the flock prior to and throughout the experimental period. Thus, seasonal changes in mating patterns and ovulation rate could be followed throughout the year without "ram effects" or pregnancy influencing interpretation of the effects of treatment on ovarian function.

At each treatment dose (i.e. high dose, low dose) a single implant was inserted to each ewe on Oct. 24, 1985. A second implant was given 4 weeks later on Nov. 21, 1985. Total treatment time was therefore 4 weeks+5 weeks=9 weeks from time of first implantation.

All animals were observed daily for oestrus.

Leparoscopic examination of all was conducted under local anaesthesia at 3 to 4 week intervals.

Figure 4:
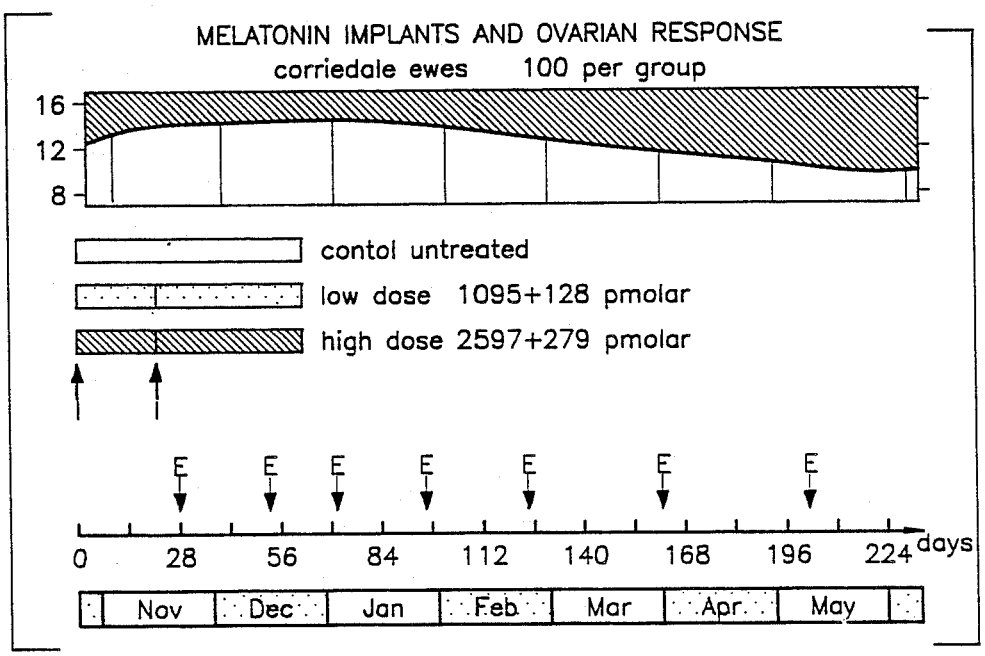

A schematic of the experimental design is shown in FIG. 4.

RESULTS

Timing of first oestrus

Figure 5:
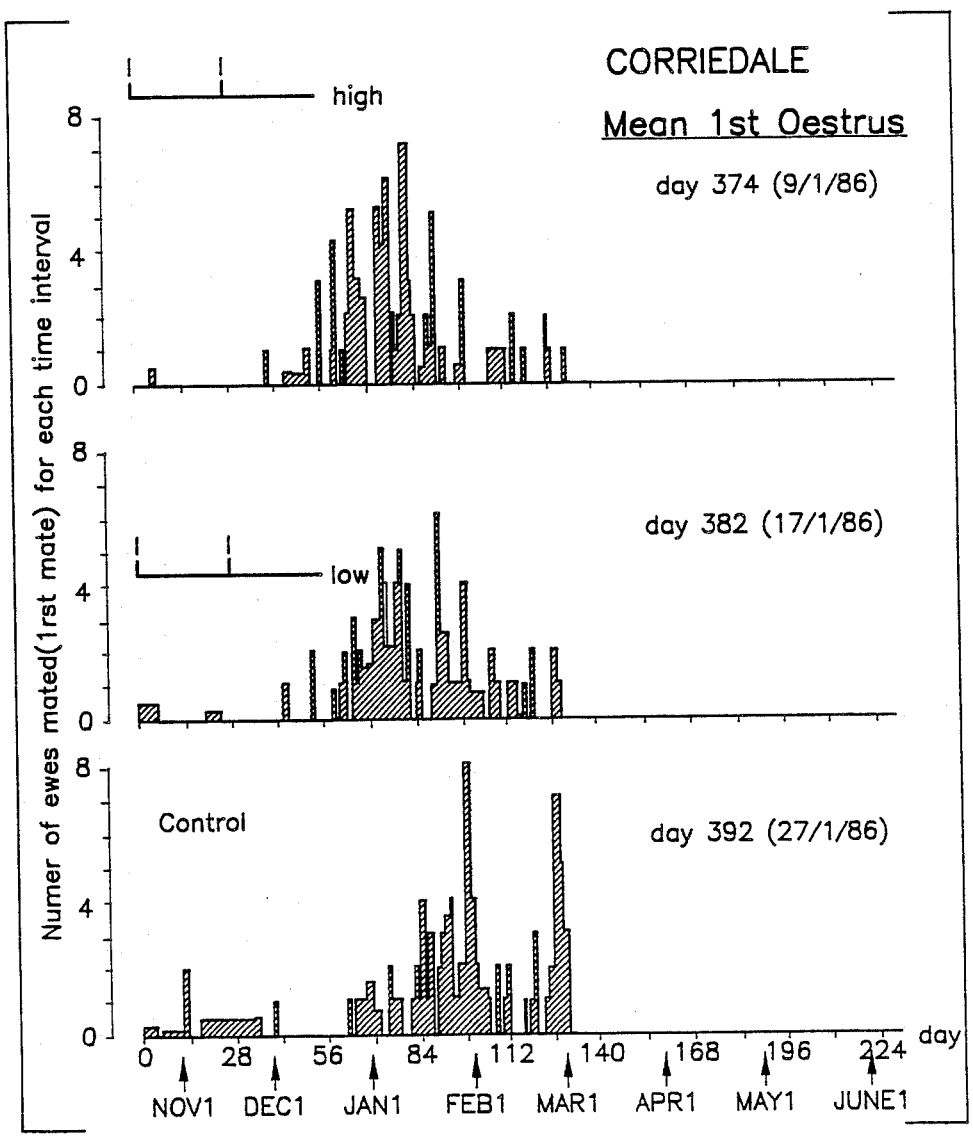

Coated implant treatment enhanced the onset of first oestrus in a dose-dependent manner. Mean first ostrus occurred on Jan. 9, 1986 for the high dose group and on Jan. 17, 1986 for the low dose group, these times being 18 and 10 days, respectively, earlier than in the untreated controls (mean 1st oestrus Jan. 27, 1986). Distribution of first oestrus is shown in FIG. 5.

Occurrence of Regular oestrus cycles

Mean cycle length (i.e. number of days between consecutive matings) was not significantly affected by treatment (Table 2).

TABLE 2

| MEAN CYCLE LENGTH IN COATED IMPLANT TREATED CORRIEDALE EWES | |
| --- | --- |
| Treatment | Cycle length (days, mean ± SEM (n)) |
| Control | 18.01 ± 0.12 (n = 360 cycles) |
| Coated Implant low dose | 18.00 ± 0.11 (n = 421 cycles) |
| Coated Implant high dose | 17.94 ± 0.12 (n = 329 cycles) |

The proportion of each flock cycling at any time was assessed by calculating the proportion of ewes cycling within 18 day "window" periods. Values determined over three sequential "windows" (i.e. proportion mating in days 1–18, 2–19, 3–20 etc.) were averaged and this average plotted against calendar date.

Figure 6:
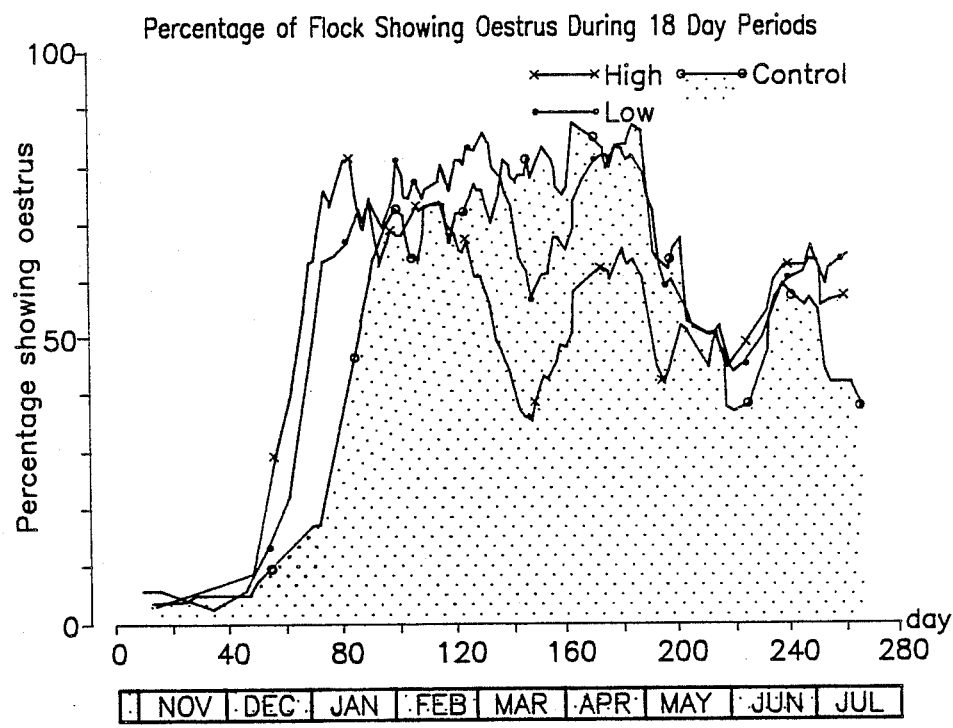

Coated implant treatment induced an early onset of regular oestrus cycles in a dose-dependent manner (FIG. 6). Regular oestrus cyclicity was maintained in both low and high dose coated implant treatments for a period of approximately 70 days following induction of cyclicity in both treated groups. Thereafter a transient decline in proportional of ewes showing regular oestrus cycles was observed. This was most marked in the high dose treatment group which showed minimum cyclicity at about 150 days from start of treatment or about 100 days from commencement of cycling. Thereafter the proportion of ewes cycling returned to normal levels until approximately 250 days from start of treatment when cyclicity in treated ewes was again greater than in control ewes (FIG. 6).

The early induction of an extended period of regular cyclicity by the coated veterinary implant according to the present invention is an important observation since treated ewes have several mating opportunities to become pregnant.

Proportion of ewes ovulating

Figure 7:
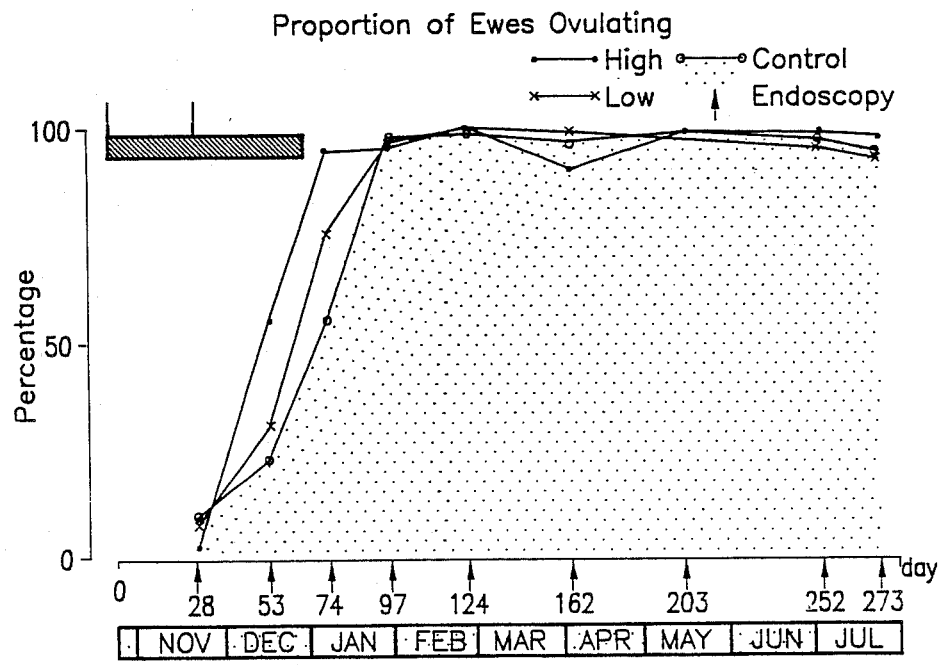

Treatment with the coated implant resulted in a dose-dependent increase in the proportion of ewes ovulating as assessed by the presence of one or more corpora lutea at endoscopy (see FIG. 7). For the high dose, the proportions ovulating on days 53 and 74 after treatment were 233% and 172% of corresponding control values (P 0.01 on a flock basis see Table 3). Ovulatory responses were dose-dependent since the lower dose induced a slightly lower increase in the proportion ovulating to 131% and 136% of control values on days 53 and 74 respectively (Table 3).

Thereafter the proportion ovulating in either group did not differ significantly from control values until 302 days after implantation at which time the proportion of ewes ovulating in the high and low dose groups, were again, above natural seasonal levels being 162% (P 0.001) and 131% (P 0.05) of control respectively (Table 3, FIG. 7).

Coated implant treatments commencing in October therefore increased the incidence of ovulation both early and late in the breeding season.

TABLE 3

DYNAMICS OF OVARIAN RESPONSE TO COATED IMPLANT PROPORTION OVULATING (%)

| | Days after start of treatment on 24th October, 1986 (Calendar date) | | | | | | | | | |
|---|---|---|---|---|---|---|---|---|---|---|
| | 28 (21/11) | 53 (16/12) | 74 (6/1) | 97 (28/1) | 124 (25/2) | 162 (3/4) | 203 (14/5) | 252 (2/7) | 273 (23/7) | 302 (21/8) |
| Control | 10.2 | $23.7^a$ | $55.2^a$ | 97.9 | 98.9 | $96.8^{xy}$ | 98.9 | 97.8 | 94.1 | $54.4^{ax}$ |
| High dose | 4.0 | $55.2^b$ | $94.7^b$ | 95.7 | 100.0 | $89.3^x$ | 98.9 | 98.9 | 97.9 | $88.0^{by}$ |
| As % of C | 39.2 | 232.9 | 171.6 | 97.8 | 101.1 | 92.3 | 100.0 | 101.1 | 103.8 | 161.8 |
| Absolute from C | −6.2 | +31.5 | +39.5 | −2.2 | +1.1 | −7.5 | 0 | +1.1 | +3.6 | +33.6 |
| Low dose | 8.0 | $31.0^a$ | $75.0^c$ | 97.0 | 100.0 | $99.0^y$ | N.E. | 94.8 | 92.8 | $71.1^{bz}$ |
| As % of C | 78.4 | 130.8 | 135.9 | 99.1 | 101.1 | 102.3 | — | 96.9 | 98.6 | 130.7 |
| Absolute from C | −2.2 | +7.3 | +19.8 | +0.9 | +1.1 | +2.2 | — | −3.0 | −1.3 | +16.7 |

$a,b,c$means with different superscripts differ significantly P < 0.01
$x,y,z$means with different superscripts differ significantly P < 0.05
N.E. = Not Endoscoped

Ovulation rate per ewe ovulating

Figure 8:
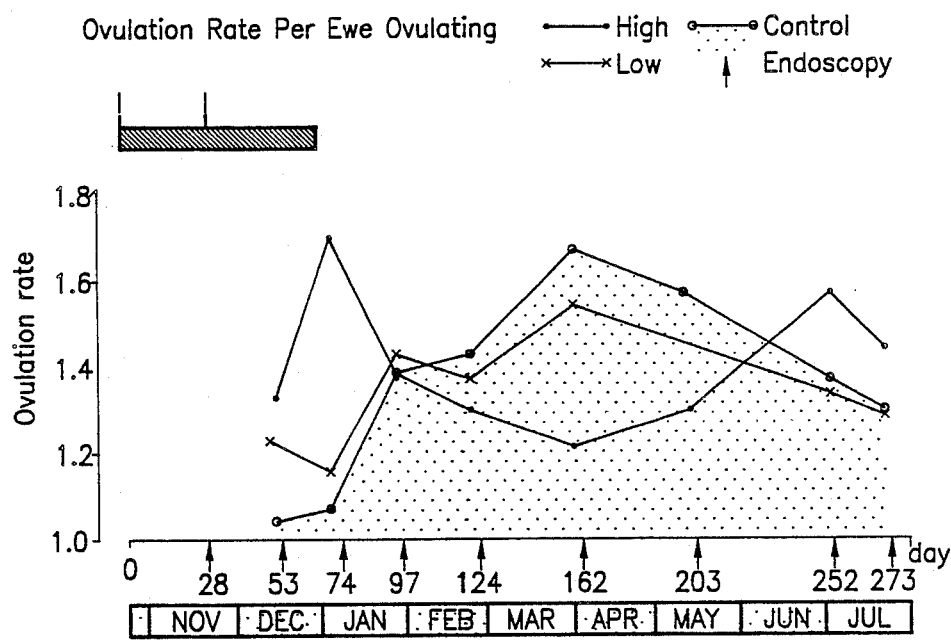

Coated implant treatments caused significant dose-dependent increases in the ovulation rate per ewe ovulating on days 53 and 74 after treatment (FIG. 8). Ovulation rates in the high and low groups were 129% and 118% of control at 53 days after start of treatment and were 157% and 107% of control at 74 days after treatment (Table 2). Thereafter ovulation rates were similar in all groups until 162-203 days after treatment when significantly lower ovulation rates were observed in the high dose group then in control. At the end of the breeding season in May and June ovulation rates in the high dose group again showed a significant increase over control (see FIG. 8 and Table 2).

TABLE 4

DYNAMICS OF OVARIAN RESPONSE TO COATED IMPLANT OVULATION RATE (CL/EWE OVULATING)

| | Days after start of treatment (date) | | | | | | | | | |
|---|---|---|---|---|---|---|---|---|---|---|
| | 28 (21/11) | 53 (16/12) | 74 (6/1) | 97 (28/1) | 124 (25/2) | 162 (3/4) | 203 (14/5) | 252 (2/7) | 273 (23/7) | 302 (21/8) |
| Control | 1.20 | $1.04^x$ | $1.08^a$ | 1.39 | 1.44 | $1.67^{ax}$ | 1.57 | $1.37^{abx}$ | 1.29 | 1.33 |
| High dose | 1.5 | $1.34^y$ | $1.70^b$ | 1.39 | 1.29 | $1.21^{by}$ | 1.30 | $1.58^{ay}$ | 1.45 | 1.37 |
| As % of C | 125.0 | 128.8 | 157.4 | 100.0 | 89.6 | 72.5 | 82.8 | 115.3 | 112.4 | 103.01 |
| Absolute from C | +0.3 | +0.3 | +0.62 | 0 | −0.15 | −0.46 | −0.27 | 0.21 | +0.16 | +0.04 |
| Low dose | 1.00 | $1.23^{xy}$ | $1.15^a$ | 1.43 | 1.38 | $1.55^{az}$ | N.E. | $1.35^{bx}$ | 1.29 | 1.28 |
| As % of C | 83.3 | 118.3 | 106.5 | 102.9 | 95.8 | 92.8 | — | 98.5 | 100.0 | 96.2 |
| Absolute from C | −0.2 | +0.19 | +0.07 | +0.04 | −0.06 | −0.12 | — | −0.02 | 0 | −0.05 |

$a,b,c$means with different superscripts differ significantly P < 0.01-0.001
$x,y,z$means with different superscripts differ significantly P < 0.05
N.E. = Not Endoscoped

TABLE 5

DISTRIBUTION OF OVULATIONS IN CONTROL AND IMPLANTED CORRIEDALE EWES AT VARIOUS TIMES AFTER START OF TREATMENT

| Days from start of treatment (day) | date | CONTROL | | | | | COATED IMPLANT HIGH DOSE | | | | | COATED IMPLANT LOW DOSE | | | | |
|---|---|---|---|---|---|---|---|---|---|---|---|---|---|---|---|---|
| | | % ewes with | | | | mean CL's per ewe | % ewes with | | | | mean CL's per ewe | % ewes with | | | | mean CL's per ewe |
| | | 0 | 1 | 2 | 3 CL | | 0 | 1 | 2 | 3 CL | | 0 | 1 | 2 | 3 CL | |
| 23 | 21/11/85 | 44 | 4 | 1 | | 0.12 | 48 | 1 | 1 | — | 0.06 | 46 | 4 | — | — | 0.08 |
| 53 | 16/12/85 | 74 | 22 | 1 | — | 0.237 | 43 | 35 | 18 | — | 0.74 | 69 | 24 | 7 | — | 0.38 |
| 74 | 6/1/86 | 43 | 49 | 4 | — | 0.552 | 4 | 39 | 48 | 3 | 1.61 | 25 | 64 | 11 | — | .0.86 |
| 97 | 28/1/86 | 2 | 56 | 36 | 1 | 1.365 | 4 | 55 | 33 | 1 | 1.33 | 2 | 55 | 41 | — | 1.384 |
| 124 | 25/2/86 | 1 | 54 | 39 | 1 | 1.42 | 1 | 65 | 27 | — | 1.28 | 1 | 80 | 39 | — | 1.38 |
| 162 | 3/4/86 | 3 | 31 | 60 | 1 | 1.62 | 9 | 66 | 18 | — | 1.085 | 1 | 47 | 44 | 4 | 1.531 |
| 203 | 14/5/86 | 1 | 43 | 44 | 4 | 1.554 | 1 | 64 | 27 | — | 1.283 | N.E. | | | | — |

TABLE 5-continued

DISTRIBUTION OF OVULATIONS IN CONTROL AND IMPLANTED CORRIEDALE EWES AT VARIOUS TIMES AFTER START OF TREATMENT

| Days from start of treatment (day) | date | CONTROL | | | | | COATED IMPLANT HIGH DOSE | | | | | COATED IMPLANT LOW DOSE | | | | |
|---|---|---|---|---|---|---|---|---|---|---|---|---|---|---|---|---|
| | | % ewes with | | | | mean CL's per ewe | % ewes with | | | | mean CL's per ewe | % ewes with | | | | mean CL's per ewe |
| | | 0 | 1 | 2 | 3 CL | | 0 | 1 | 2 | 3 CL | | 0 | 1 | 2 | 3 CL | |
| 252 | 2/7/86 | 2 | 56 | 33 | — | 1.341 | 1 | 39 | 46 | 2 | 1.557 | 5 | 60 | 32 | — | 1.278 |
| 273 | 23/7/86 | 5 | 56 | 23 | — | 1.214 | 2 | 48 | 37 | 1 | 1.42 | 7 | 64 | 26 | — | 1.196 |
| 302 | 21/8/86 | 41 | 33 | 16 | — | 0.722 | 10 | 46 | 27 | — | 1.205 | 28 | 50 | 19 | — | 0.907 |

The results show that coated implant treatment caused an early onset to the seasonal pattern of ovulation rate. The changes in ovulation rate were entirely due to an increased occurrence of twin ovulations in the treated groups. No evidence for supraphysiological ovulation patterns (e.g. litters 3) was found (see Table 5).

These results demonstrate that coated implant treatment brings forward the normal seasonal pattern in ovulation rate in Corriedale ewes. Peak ovulation rates following treatment did not exceed the normal seasonal maximum but were shown to occur approximately 88 days (3 months) earlier in the year.

Example 9

Field Trials 3a, 3b, 3c

The purpose of this series of experiments was to evaluate the effect of coated implants prepared as in Example 1 on the reproductive performance of different breeds of ewes, when those ewes were joined with fertile rams at times of the year earlier than their normal reproductive peak. Treatments commencing at the optimum treatment strategy for the practical use of these implants in various breeds.

The joining times selected for these trials in Merino, BL×M and Romney flocks are therefore appropriate to test the sensible application of the coated implant treatment under industry conditions.

Joining times and locations of the trials were as follows:

Trial 3a: Merino (maiden 1± year old); joined: 8/11/85, Location: Little River Vic.

Trial 3b: BL×M (parous, mature, 3–4 yr); joined: 18/11/85, Location: Ballan, Vic.

Trial 3c: Romney (parous, mature 2–8 yr); joined: 28/1/86, Location: Camberdown, Vic.

Treatment strategies tested were designed to determine the effects of a single implant or a sequence of two implants. Further, with either dosage or regimen, the experiments were designed to determine the effects of changing the time between administration of the implants and introduction of the rams.

For the sequential implant treatments a second implant was inserted 28 days after the first. Since a single implant has a delivery phase of approximately 5–6 weeks the treatment durations following a sequence of two implants administered 4 weeks apart is at least 9 weeks.

Figure 9:
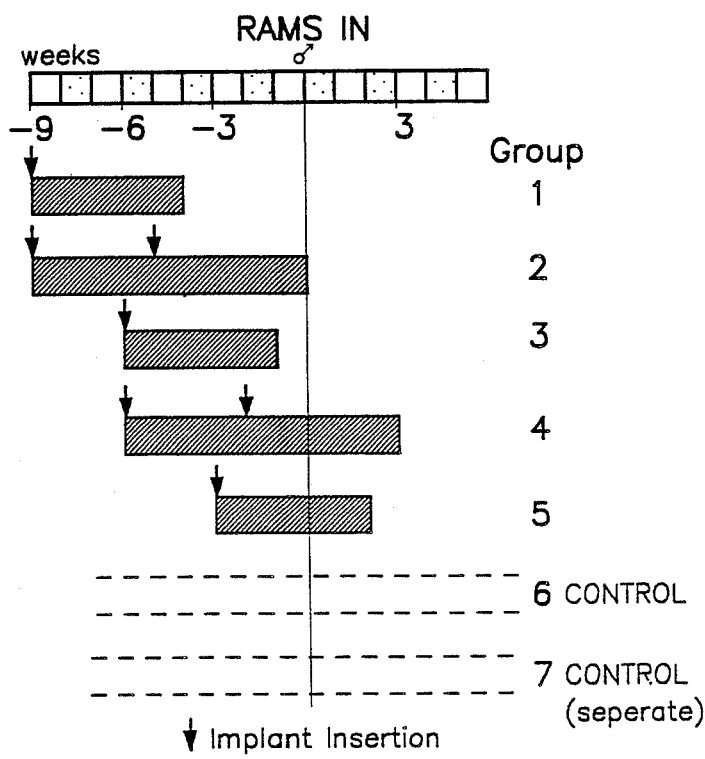

A schematic representation of the trial design is given in FIG. 9. Two types of control (untreated) group were included. The first control was run with all the treated ewes at joining while a second control group was joined in isolation from the main mating mob. This was necessary in order to assess the effects of ewe-ewe interactions on the mating and conceptio patterns. Treatments are summarized as follows:

GROUP 1 : Commencing 9 weeks before joining, duration of about 9 weeks.

2 : Commencing 9 weeks before joining, duration of about 5 weeks.

3 : Commencing 6 weeks before joining, duration of about 9 weeks.

4 : Commencing 6 weeks before joining, duration of about 5 weeks.

5 : Commencing 3 weeks before joining, duration of about 5 weeks.

6 : Control untreated ewes run with all treatment groups at joining.

7 : Control untreated ewes joined at the same time as other groups but maintained in isolation from the other mating groups.

RESULTS

Field Trial 3a

Figure 10:
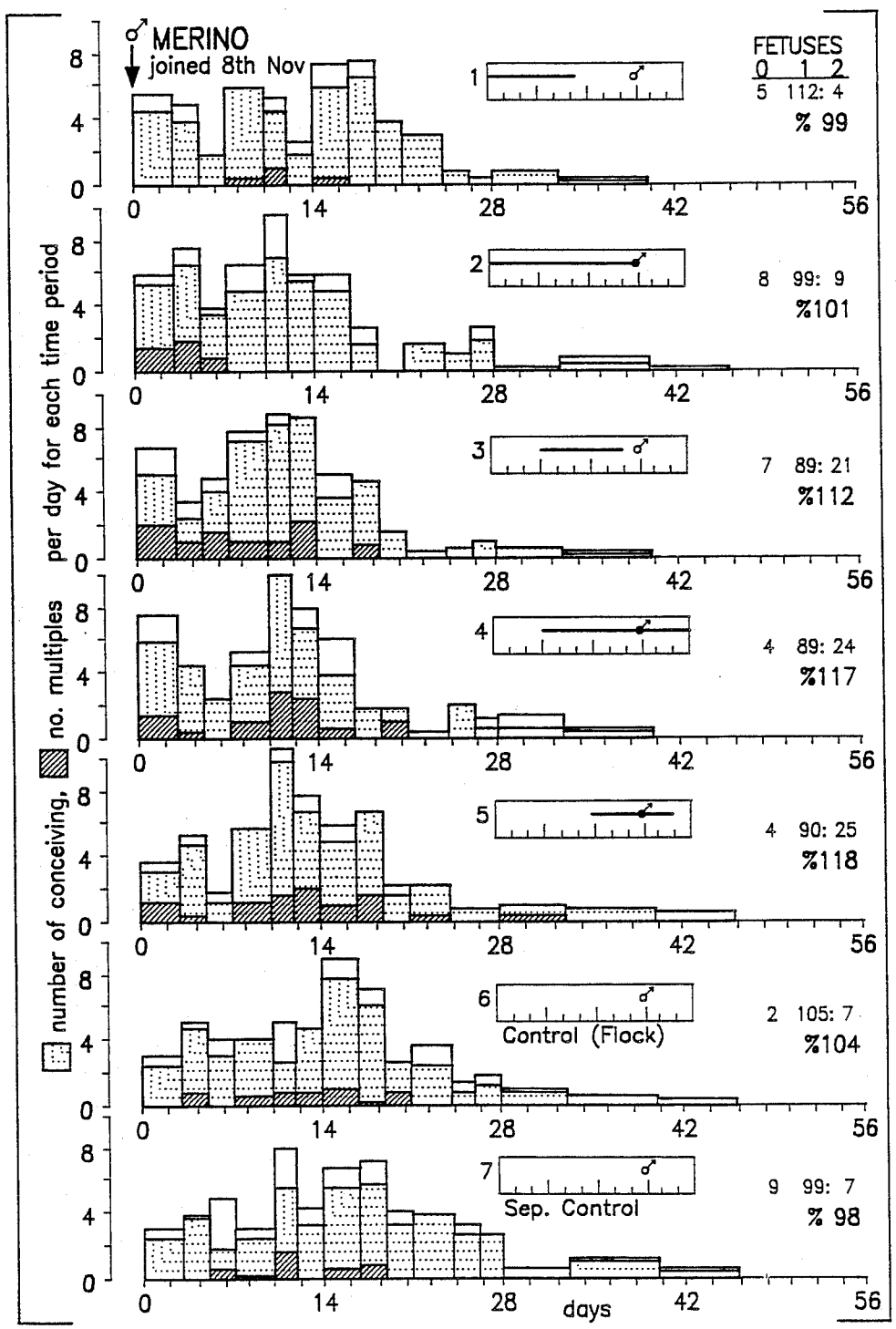

Optimization of coated implant treatments in MAIDEN MERINO EWES joined in Sorino Onset of oestrus and conception patterns Treatment of maiden Merino ewes with melatonin implants prior to joining on November 8th induced only minor changes in the occurrence of oestrus see FIG. 10 and Table 8. Although the proportion of treated ewes (Groups 2,3,4 and 5 in Table 6) mating during the first 14 days was significantly higher (P 0.05) than in control groups (Groups 6 and 7), the mean time from joining to conception in the treated groups was only shortened by 3 to 5 days compared with the separate control groups (see Table 7).

The main reason for there being little effect of treatment on conception patterns in the maiden Merino groups was because many of these ewes were already cycling at the time when rams were introduced in early November (note occurrence of matings immediately after ram introduction in Group 7, FIG. 7). Thus coated implant treatment could not substantially shorten the mean interval from joining to conception in this flock.

Fertility and Fecundity following coated implant treatments

Fertility of the maiden Merino ewes used in this trial was very high. Mid pregnancy ultrasound measurements indicated that 90.4–98.2% of ewes were pregnant in the control group. Treatment with coated implant had no significant effect on the proportion of animals pregnant (Table 7). Moreover, most ewes in this flock conceived to first service regardless of treatment (FIG. 10).

In marked contrast, fecundity was significantly affected by treatment (FIG. 10, Table 7). Expected lambing percentage (i.e. fetuses/ewe in group) were 98 and 104% in control groups 6 and 7 respectively. These values are extremely high for maiden Merino ewes which have a national average fecundity in the range of 60%. Despite the high starting point in the control flocks, the coated implant treatment significantly enhanced expected lambing percentages.

Example 9

Field Trial 36

TABLE 6

OCCURRENCE OF CONCEPTIONS AT VARIOUS TIMES AFTER JOINING (DAY 0) FOR EWES RECEIVING DIFFERENT COATED IMPLANT TREATMENTS
MAIDEN MERINO EWES

| Group | T | n in Group | No. conceiving at each time point (days after joining) | | | | | | | | |
|---|---|---|---|---|---|---|---|---|---|---|---|
| | | | 0-7 | 8-14 | 0-14 | 15-21 | 0-21 | 22-28 | 0-28 | 29-40 | 0.40 |
| 1 | −9,5 | 121 | $26^{abc}$ | $31^b$ | $57^{bc}$ | $39^a$ | $96^{abc}$ | $13^{ab}$ | 109 | 6 | $115^{ab}$ |
| 2 | −9,9 | 116 | $36^a$ | $40^{ab}$ | $76^a$ | $18^c$ | $94^{ab}$ | $11^{abc}$ | 105 | 3 | $108^{ab}$ |
| 3 | −6,5 | 117 | $28^{abc}$ | $54^a$ | $82^a$ | $22^{bc}$ | $104^a$ | $3^c$ | 107 | 5 | $112^{ab}$ |
| 4 | −6,9 | 117 | $32^{ab}$ | $48^a$ | $80^a$ | $20^{bc}$ | $100^{ab}$ | $7^{bc}$ | 107 | 7 | $114^a$ |
| 5 | −3,5 | 119 | $20^{bc}$ | $50^a$ | $70^{ab}$ | $30^{abc}$ | $100^{ab}$ | $7^{bc}$ | 107 | 6 | $113^{ab}$ |
| 6 | C | 114 | $22^{abc}$ | $26^b$ | $48^c$ | $40^a$ | $88^{bc}$ | $13^{ab}$ | 101 | 6 | $107^{ab}$ |
| 7 | Sep C. | 115 | $18^c$ | $27^b$ | $45^c$ | $33^{ab}$ | $78^c$ | $21^a$ | 99 | 5 | $104^b$ |

Values with different superscripts differ significantly, $P < 0.05$

TABLE 7

FECUNDITY AND MEAN CONCEPTION DATES IN MAIDEN MERINO EWES WHICH RECEIVED VARIOUS COATED IMPLANT TREATMENTS PRIOR TO JOINING ON 8 NOVEMBER.

| GROUP | NUMBER SCANNED | 0 | SINGLE | TWIN | TRIP | FETUSES/100 EWE IN GROUP | REL. TO GR.7. | MEAN CONC. DATE (1985) | DAYS AFTER JOINING |
|---|---|---|---|---|---|---|---|---|---|
| 1 | 121 | 5 | 112 | 4 | 0 | $99.2^c$ | 1.009 | 327 | 15 |
| 2 | 116 | 8 | 99 | 9 | 0 | $100.9^{bc}$ | 1,026 | 325 | 13 |
| 3 | 117 | 7 | 89 | 21 | 0 | $112.0^{ab}$ | 1.139 | 325 | 13 |
| 4 | 117 | 4 | 89 | 24 | 0 | $117.1^a$ | 1.191 | 325 | 13 |
| 5 | 119 | 4 | 90 | 25 | 0 | $117.6^a$ | 1.196 | 327 | 15 |
| 6 | 114 | 2 | 105 | 7 | 0 | $104.4^{bc}$ | 1.062 | 329 | 17 |
| 7 | 115 | 9 | 99 | 7 | 0 | $98.3^c$ | 1.000 | 330 | 18 |

Values with different superscripts differ significantly $P < 0.05$

Treatments commencing 3 or 6 weeks prior to joining significantly (P 0.05-0.01) increased expected lambing percentage to 112-118%. These changes represent increases of up to 19.6% relative to the separate control flock (see Table 9). Best results were obtained with treatments starting 6 weeks prior to joining and lasting for about 9 weeks (e.g. Group 4) or starting 3 weeks prior to joining and lasting for about 5 weeks (i.e. single implant treatment, Group 5). Treatments commencing more than 6 weeks before joining were ineffective.

The results indicate that a single implant or a sequence of two implants first administered 3-6 weeks prior to joining will significantly increase fecundity in November joined maiden Merino ewes by approximately 20% relative to untreated controls.

Litter size distribution

Figure 11:
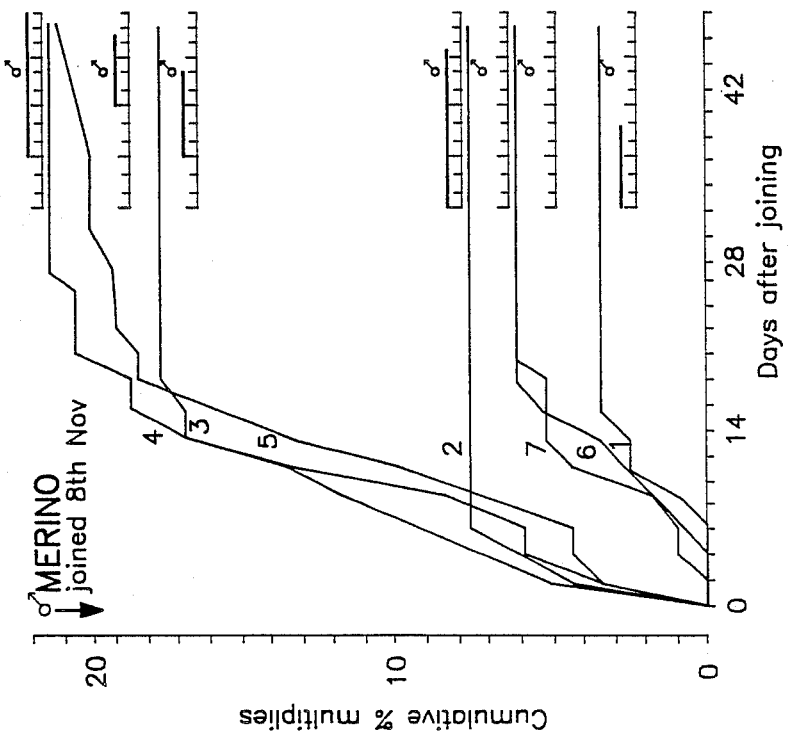

The increase in expected lambing percentage was due primarily to the occurrence of twin fetuses (Table 9). The occurrence of twins throughout the joining period is shown by the black portion of histograms in FIG. 10 and a cumulative occurrence of multiples is shown in FIG. 11.

Figure 12:
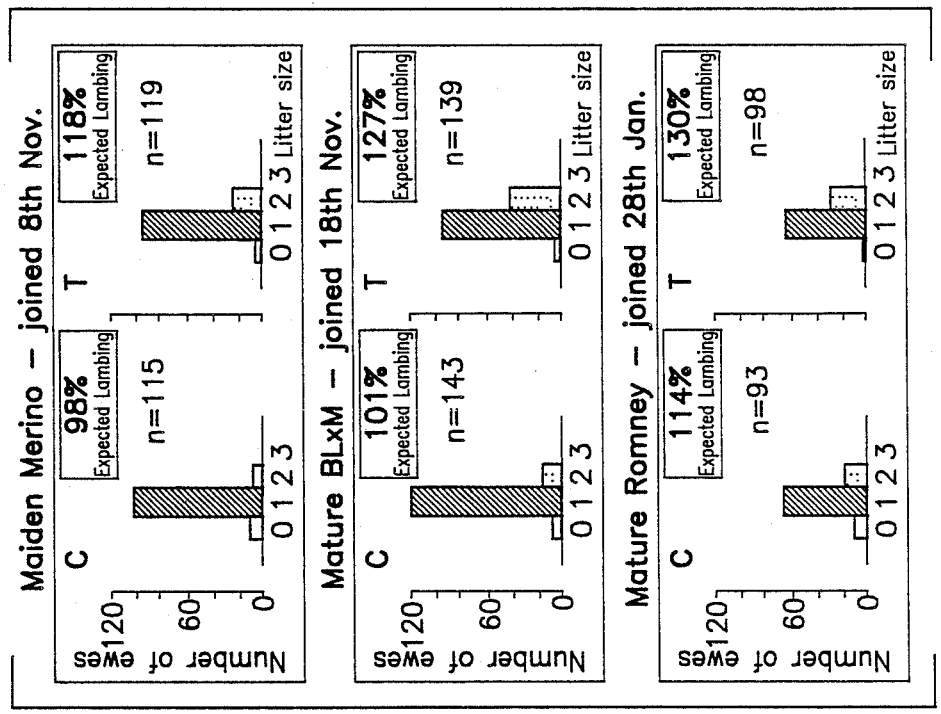

This is important since the artificial induction of increased lambing percentages by presently available techniques tends to cause superovulation, which is undesirable on several different grounds. That Melatonin, unexpectedly, does not induce superovulation is apparent from the data in FIG. 12a.

OPTIMIZATION OF COATED IMPLANT TREATMENTS IN BORDER LEICESTER×MERINO EWES JOINED IN SPRING

Onset of oestrus and conception patterns in BL×M ewes

Border Leicester×Merino flocks joined in Spring frequently show mating patterns characteristic of ram induced matings. That is, the sudden introduction of rams induces a silent ovulation within 2 days and the first overt oestrus occurs one cycle later at about 20-22 days. The effect is not always reliable.

Figure 13:
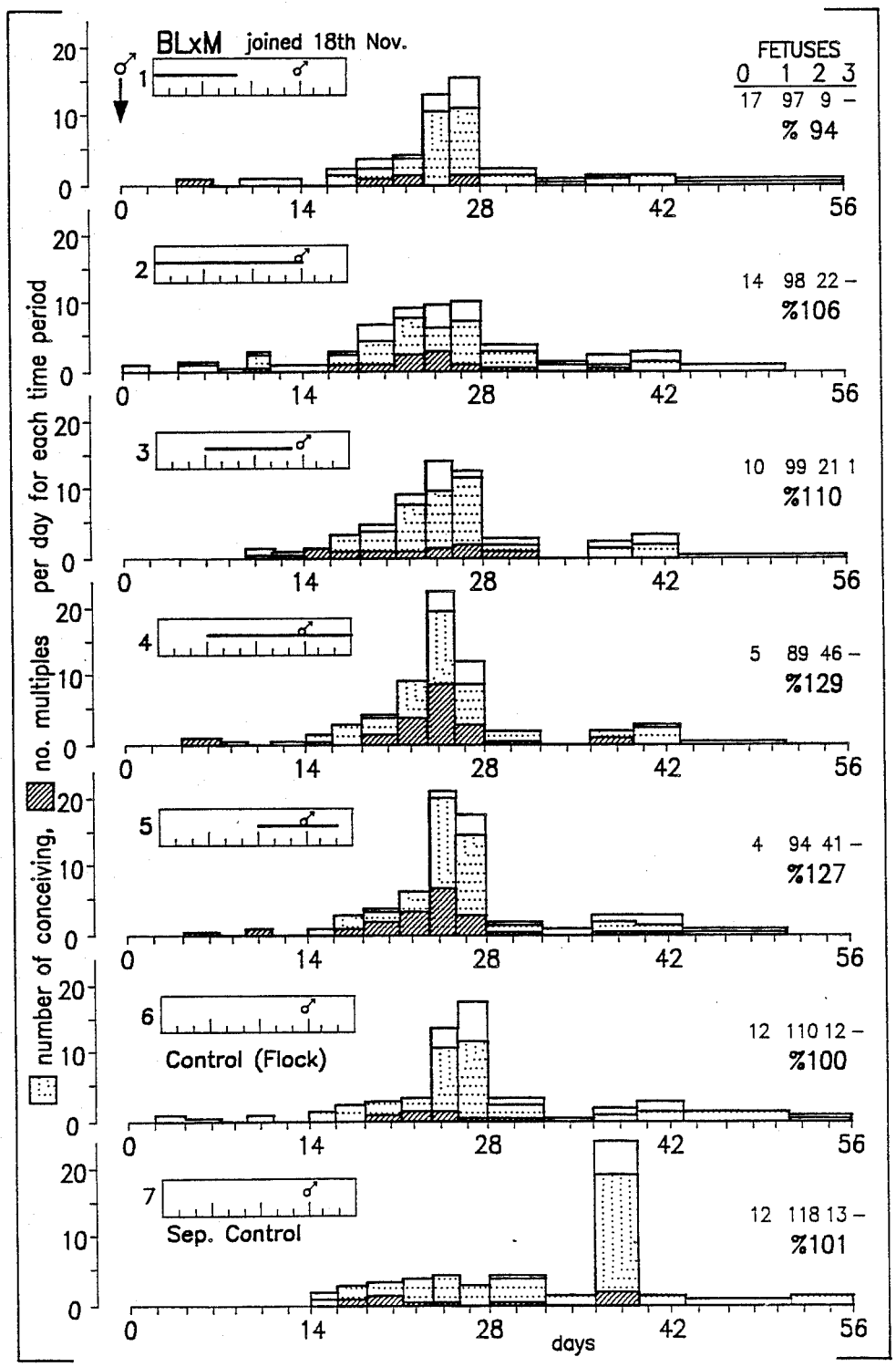

In the BL×M trial a poor response to "ram effect" was seen in the separate control group joined on November 18th (see group 7, FIG. 13). In this separate control group, which is the true control for the natural mating patterns which this farmer achieved without coated implant treatment, a peak of matings was observed at 36-39 days after ram introduction. This is one cycle (i.e. approximately 18 days) after the expected peak of matings if "ram effect" was operative in this flock. Mean conception date for this control flock was 36 days after joining (see also Table 8).

Coated implant treatments which commenced 3 or 6 weeks prior to joining rendered the BL×M ewes responsive to "ram effect" so that peak incidence of matings was observed at about 24 days after joining (FIG. 13). By 28 days after joining, significantly more ewes had mated in the coated implant treated flocks than in the separate control flock (Table 8). Mean time from joining to conception was reduced from 36 days in the control flock to 27 to 28 days in the treated groups (Table 9).

For treatments commencing 3 to 6 weeks prior to joining there were no substantial differences in the mating and conception patterns during the first 28 days of joining regardless of whether the treatment was for 5 or 9 weeks duration (Table 8, FIG. 13).

treated were in a declining phase of ovarian response at th time of joining. Fertility (no of ewes conceiving) was not significantly affected by coated implant treatment

TABLE 8

OCCURRENCE OF CONCEPTIONS AT VARIOUS TIMES AFTER JOINING (DAY 0)
FOR EWES RECEIVING DIFFERENT COATED IMPLANT TREATMENTS
MATURE - BORDER LEICESTER X MERINO EWES

| GROUP | T | No. in group | Number conceiving at each time point (days after joining) | | | | | | | | | | |
|---|---|---|---|---|---|---|---|---|---|---|---|---|---|
| | | | 0–7 | 8–14 | 0–14 | 15–21 | 0–21 | 22–28 | 0–28 | 29–43 | 0–43 | 44–55 | 0–56 |
| 1 | −9,5 | 123 | 2 | $3^{ab}$ | $5^{ab}$ | 11 | $16^b$ | $62^{bc}$ | $78^c$ | $18^b$ | $96^c$ | $10^{ab}$ | $106^b$ |
| 2 | −9,9 | 134 | 6 | $9^a$ | $15^a$ | 21 | $36^a$ | $63^c$ | $89^{bc}$ | $26^b$ | $115^{bc}$ | $5^{abc}$ | $120^b$ |
| 3 | −6,5 | 131 | — | $5^{ab}$ | $5^b$ | 19 | $24^{ab}$ | $73^b$ | $97^{abc}$ | $18^b$ | $115^{bc}$ | $5^{abc}$ | $120^{ab}$ |
| 4 | −6,9 | 140 | 2 | — | $2^b$ | 20 | $22^b$ | $86^{ab}$ | $108^{ab}$ | $23^b$ | $131^{ab}$ | $44^{bc}$ | $135^a$ |
| 5 | −3,5 | 139 | 1 | $1^b$ | $2^b$ | 13 | $15^b$ | $95^a$ | $110^a$ | $24^b$ | $134^a$ | $1^c$ | $135^a$ |
| 6 | C | 134 | 1 | $2^{ab}$ | $3^b$ | 16 | $19^b$ | $67^{bc}$ | $86^c$ | $23^b$ | $109^c$ | $13^a$ | $122^{ab}$ |
| 7 | Sep C | 143 | — | — | — | 16 | $16^b$ | $23^d$ | $39^d$ | $84^a$ | $123^{bc}$ | $8^{abc}$ | $131^{ab}$ |

Values with different superscripts differ significantly, $P < 0.05$

TABLE 9

FECUNDITY AND MEAN CONCEPTION DATES IN MATURE BORDER LEICESTER X MERINO EWES WHICH
RECEIVED VARIOUS COATED IMPLANT TREATMENTS PRIOR TO JOINING ON 18 NOVEMBER.

| GROUP | NUMBER SCANNED | 0 | SINGLE | TWIN | TRIP | FETUSES/100 EWE IN GROUP | REL. TO GR.7. | MEAN CONC. DATE (1985) | DAYS AFTER JOINING |
|---|---|---|---|---|---|---|---|---|---|
| 1 | 123 | 17 | 97 | 9 | — | $93.5^c$ | 0.929 | 351 | 30 |
| 2 | 134 | 14 | 98 | 22 | — | $106.0^{bc}$ | 1.053 | 348 | 26 |
| 3 | 131 | 10 | 99 | 21 | — | $109.9^b$ | 1.091 | 349 | 27 |
| 4 | 140 | 5 | 89 | 46 | — | $129.3^a$ | 1.284 | 49 | 27 |
| 5 | 139 | 4 | 94 | 41 | — | $126.6^a$ | 1.257 | 350 | 28 |
| 6 | 134 | 12 | 110 | 12 | — | $100.0^{bc}$ | 0.993 | 352 | 30 |
| 7 | 143 | 12 | 118 | 13 | — | $110.7^{bc}$ | 1.000 | 356 | 34 |

Values with different superscripts differ significantly, $P < 0.05$.

For the 2 implant (i.e. 9 week duration) treatments which commenced prior to 6 weeks before joining (i.e. at −9 weeks) significantly more ewes conceived during the immediate post joining period (Table 8) but overall the distribution of matings and conceptions was broader than for other treatment groups.

Optimum conception patterns were achieved with treatments commencing 3 to 6 weeks prior to joining. Treatments of one implant or two implants administered sequentially were essentially equivalent. On practical grounds a single implant treatment commencing 3 to 6 weeks prior to joining was shown to be optimal for achieving a defined early joining in BL×M ewes.

Fertility and fecundity following coated implant treatment of BL×M ewes

The incidence of twinning was low (less than 10% twins) in control flocks (Table 9) as expected. This is consistent with Spring joining at which time the ovulation rate is near its seasonal nadir. As in the Merino Field Trial (3a), the increase in flock fecundity (fetus-/ewe in group) was due to there being fewer non-pregnant ewes and to increased fecundity of the ewes lambing. As previously, the treatments at 3–6 weeks prior to joining induced an improvement in flock performance early in the season such the treated animals were performing as they would at their natural peak of reproductive activity. As can be seen from FIG. 12b, superovulation (leading to triplets/quads/etc) was not induced.

Treatment with coated implant 3 to 6 weeks prior to joining substantially increased expected lambing percentages from 100 to 101% in control flocks to 110 to 129% in the treated flocks (Table 9, FIG. 13). The increase was greatest for the single implant treatments commencing 3 weeks prior to joining where increases relative to the separate control flock were 26 to 29%.

Treatments commencing 9 weeks prior to joining resulted in poor responses (FIG. 13) since ewes thus although the number of non-pregnant animals was lower in the coated implant treated groups 4 and 5. (FIG. 13, Table 9).

Example 9

Field Trial 3c

OPTIMIZATION OF COATED IMPLANT TREATMENTS FOR MATURE ROMNEY EWES JOINED IN JANUARY

Onset of oestrus and conception patterns in Romney ewes

Romney ewes (like other highly seasonal British breeds in the Southern Hemisphere) joined in January to February are usually unresponsive to ram effect so that no synchronized mating patterns are expected at about 20 to 22 days following introduction of the rams. Instead mating and conception patterns are typically very extended and this reflects the gradual commencement of cyclic activity for this breed during March. For these breeds it is a particular problem to reliably obtain matings prior to March.

Figure 14:
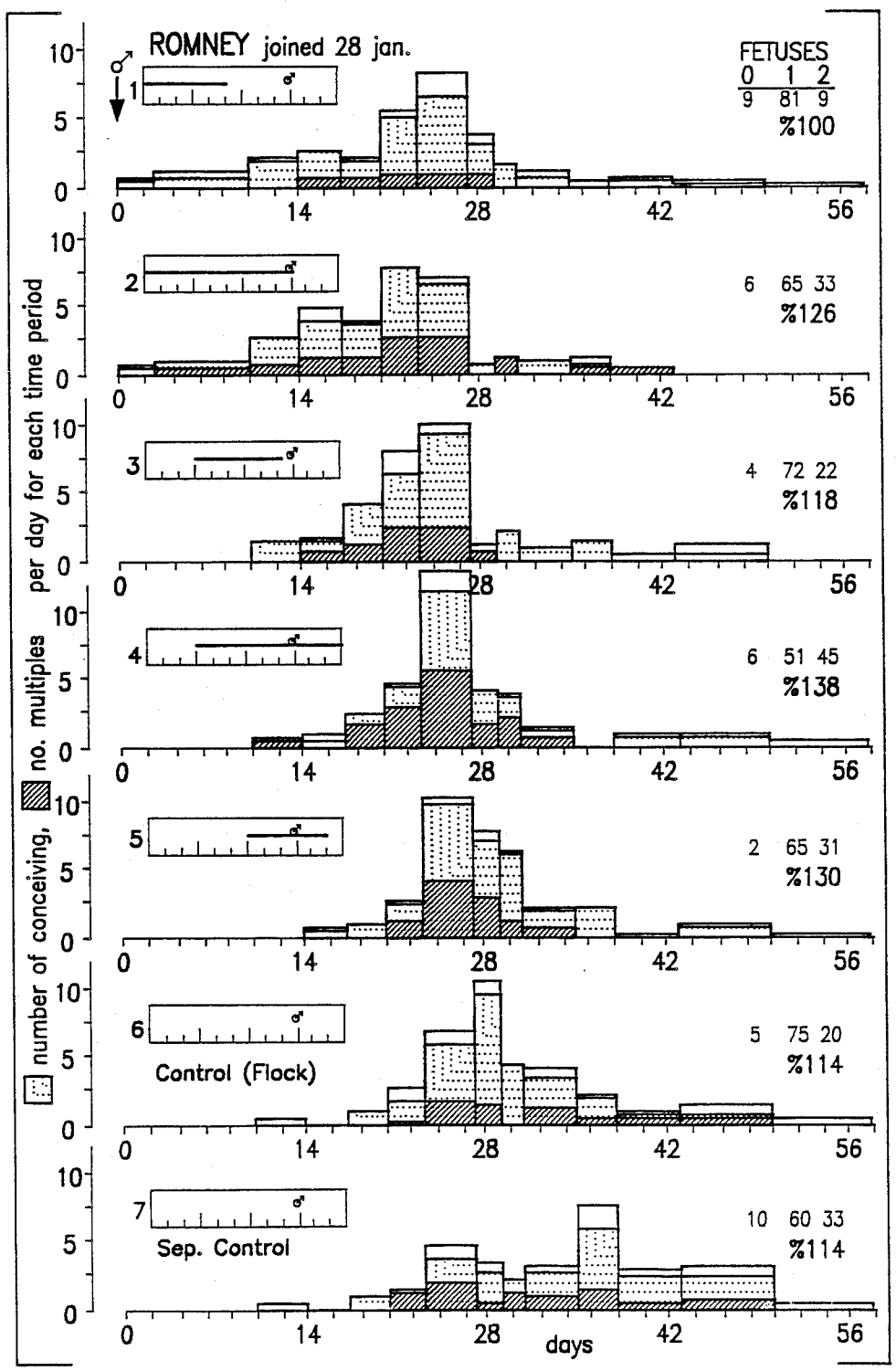

The data from the Romney field trial amply substantiate this point since very few ewes in the separate control group mated during the first month following a late January joining (see group 7, FIG. 14). The proportion of ewes mated in the separate control group was significantly lower than in all treated groups at 4, 5 and 6 weeks after joining (Table 10). Mean time from joining to conception in the separate control group was 37 days.

Treatment with coated implant at 3 to 6 weeks prior to joining rendered these ewes responsive to "ram effect" so that matings and conceptions occurred primarily during a period centered around 22 days after joining (FIG. 14, Table 10).

Greatest definition of joining period was obtained with coated implant treatments commencing 3 to 6 weeks prior to joining. Mean time from joining to conception in these groups was 26 to 30 days (Table 11).

As in the Merino Field Trial (3a), the increase in flock fecundity (fetus/ewe in group) was due to there being fewer non-pregnant ewes and to increased fecundity of the ewes lambing. As previously, the treatments at 3-6 weeks prior to joining induced an improvement in flock performance early in the season such the treated animals were performing as they would at their natural peak of reproductive activity. As can be seen from FIG. 12c, superovulation (leading to triplets/quads/etc) was not induced.

Example 10

Field Trial 4

Effectiveness of treatments with coated melatonin implants administered at different times of the year This experiment was conducted to show that the application of the implants to control seasonal breeding patterns is appropriate at different times of the year. The trial was conducted at Rutherglen, Victoria, Australia.

A treatment consisting of a sequence of two implants of a type described in Example 1 was given to five separate groups of 100 Border Leicester×Merino cross ewes. The treatment consisted of the administration of two implants, the first at six weeks and the second at two weeks before joining. Joining times for the five treatment groups were at six week intervals, thus: September 30, November 11, December 23, February 3 and March 10. These joining times were chosen to assess the effectiveness of treatment in this breed at times ranging from the seasonal minimum of reproductive performance (August-September) to the seasonal maximum around March. Five control (untreated) groups (n=100/group) were joined with the treated groups.

Figure 15:
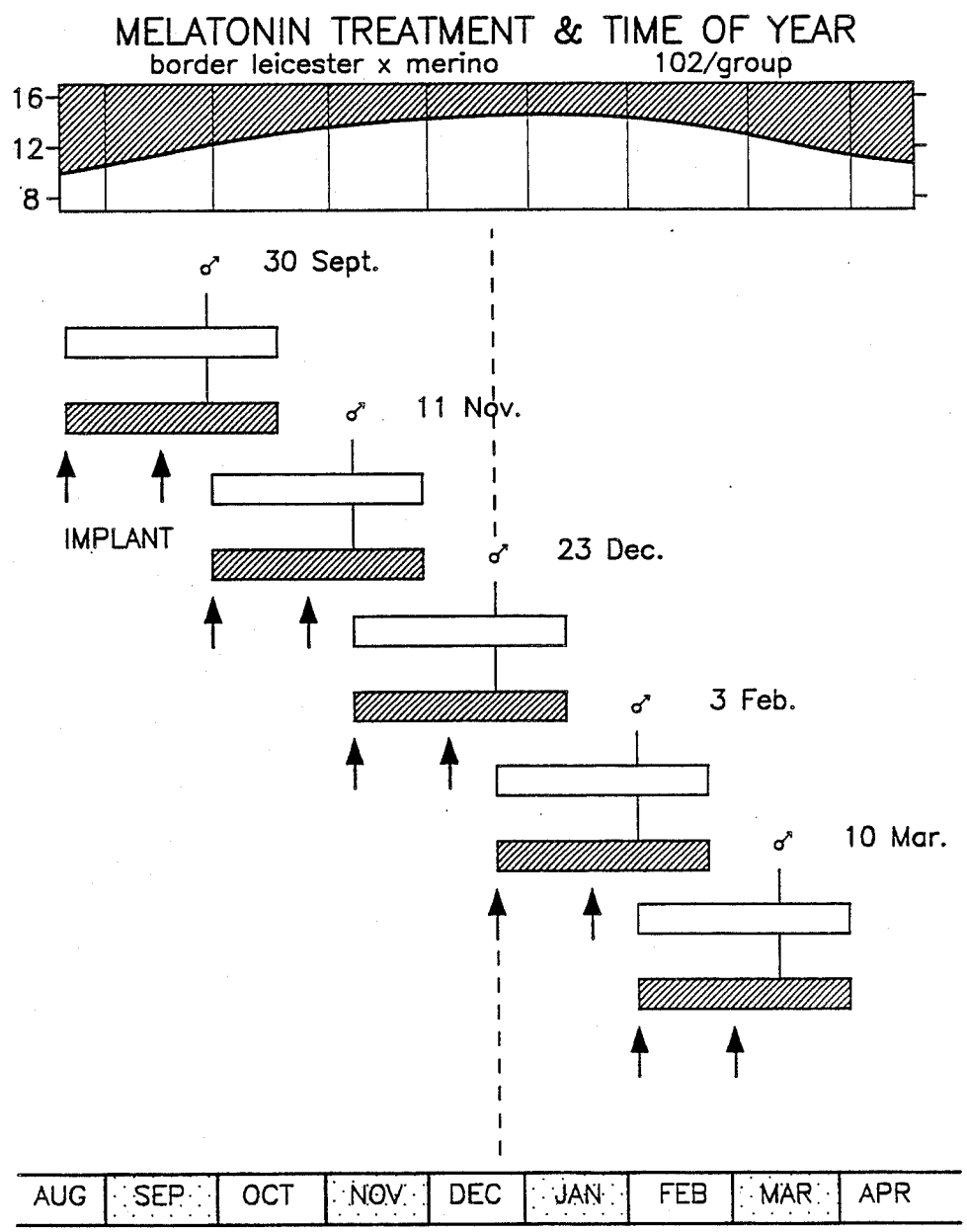

A schematic of the experiment design is shown in FIG. 15.

RESULTS

Field Trial 4

(a) Onset of oestrus and conception patterns

Figure 16:
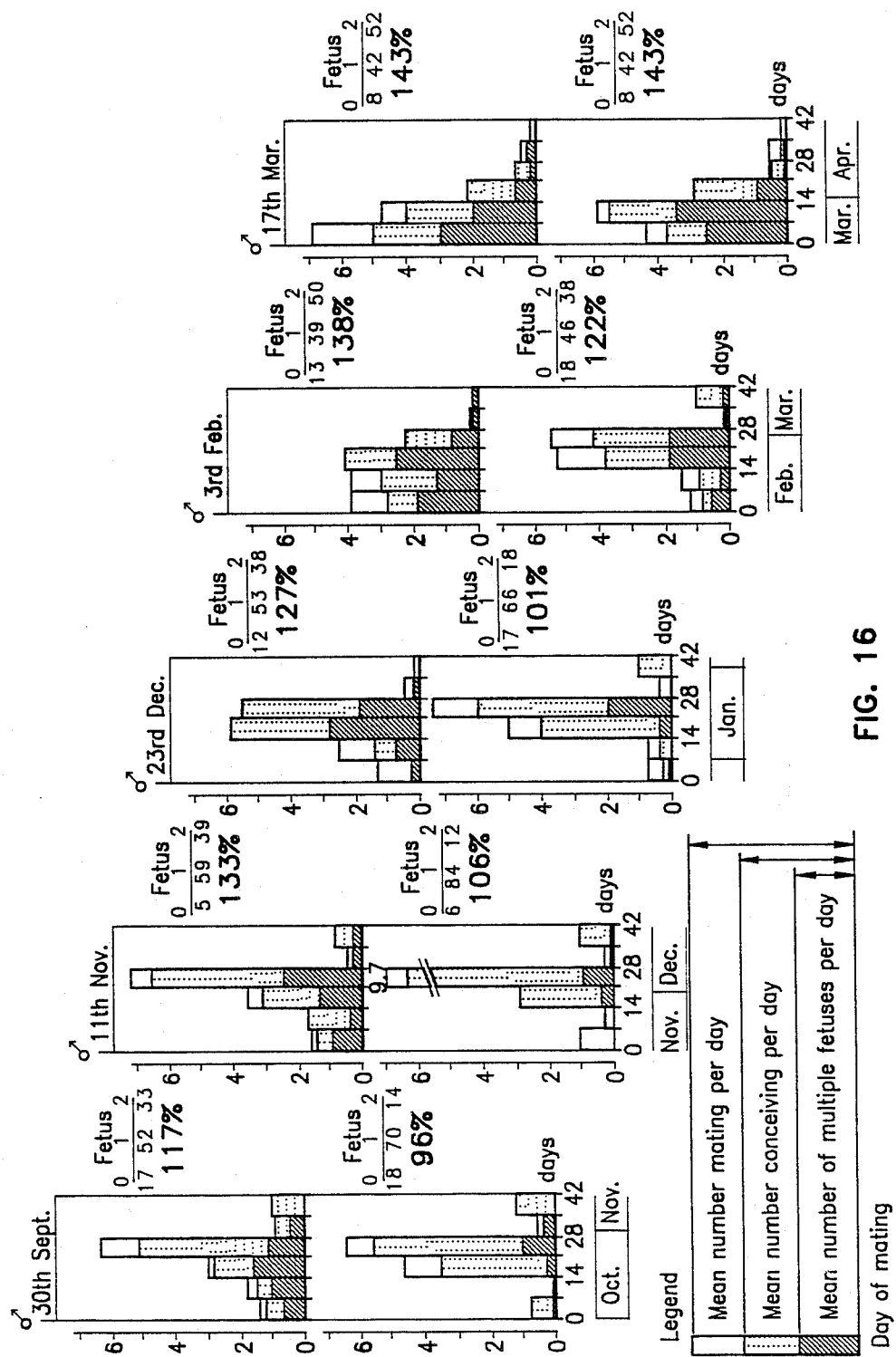

For joining times between late September and late December, conception patterns in both treated and control groups were characteristic of those expected from a "ram induced" onset to cyclicity with most matings occurring at between 14-28 days after introduction of the rams (FIG. 16). Slightly more ewes mated early in the treated groups. For the Rutherglen area "ram effect" is generally regarded as unreliable in flocks joined in September-October, but since both treated and control groups were mated as one mob in this experiment it is very likely that control ewes were induced into cyclicity by exposure to oestrus ewes in the treated groups (i.e. ewe-ewe effects). Thus, for the September joined control group, the mating patterns are likely to have been improved by indirect social facilitation effects of implant treatments.

At later joining times (e.g. February and March) an increasing proportion of ewes were cycling at the time of ram introduction (FIG. 16).

(b) Fertility and fecundity following implant treatments at different times of the year Implant treatment significantly (P 0.01-0.001) enhanced the fecundity of BL×M ewes joined in September, November and December with from 20-26 extra fetuses per 100 ewes joined at these times (Table 12 and FIG. 16). These changes represented relative increases in expected lambing percentage of 21% for late September joining, 26% for November joining and 26% for December joining flocks (Table 12).

Treatments which commenced at the summer solstice in late December for a joining in early February also increased the number of lambs expected per 100 ewes by 17, but since control flocks lambing percentages were high at this time, the relative improvement in fecundity due to treatment was a non-significant 14% relative increase from control (Table 12).

As control reached peak reproductive performance in March, the implant treatment became less effective so that fecundity in March joined ewes was not significantly affected by treatment.

The increase in fecundity due to treatment was almost entirely due to an increased occurrence of wins (Table 12). There was no evidence for supraphysiological boosts to ovulation rate (i.e. litters 2) for ewes treated at any time. Fertility was not affected by implant treatment.

The data indicates that implant may be used effectively to improve fecundity in BL×M ewes in the Southern Hemisphere for all joining times from late September to early February.

The treatment can therefore be recommended for spring and summer joinings, especially for all breeds which are responsive to ram effect at these times.

TABLE 10

OCCURRENCE OF CONCEPTIONS AT VARIOUS TIMES AFTER JOINING (DAY 0) FOR EWES RECEIVING DIFFERENT COATED IMPLANT TREATMENTS MATURE ROMNEY EWES

| GROUP | T | No. in group | Number conceiving at each time point (days after joining) | | | | | | | | | |
|---|---|---|---|---|---|---|---|---|---|---|---|---|
| | | | 0-14 | 15-20 | 0-20 | 21-27 | 0-27 | 28-35 | 0-35 | 36-43 | 0-43 | 44-58 | 0-58 |
| 1 | −9,5 | 99 | $16^a$ | $13^{ab}$ | $29^{ab}$ | $41^b$ | $70^b$ | $14^{bcd}$ | $84^{ab}$ | $3^b$ | $87^{ab}$ | $3^c$ | $90^{ab}$ |
| 2 | −9,9 | 103 | $16^a$ | $22^{ab}$ | $38^a$ | $49^{ab}$ | $87^a$ | $6^d$ | $93^a$ | $4^b$ | $97^a$ | $1^c$ | $98^{ab}$ |
| 3 | −6,5 | 98 | $5^b$ | $17^{ab}$ | $22^b$ | $56^a$ | $78^{ab}$ | $9^{cd}$ | $87^a$ | $5^b$ | $92^a$ | $2^c$ | $94^{ab}$ |
| 4 | −6,9 | 102 | $2^b$ | $8^{bc}$ | $10^c$ | $59^{a'}$ | $69^b$ | $20^{bc}$ | $89^a$ | $3^b$ | $92^{ab}$ | $4^{bc}$ | $96^{ab}$ |
| 5 | −3,5 | 98 | — | $3^c$ | $3^c$ | $48^{ab}$ | $51^c$ | $33^a$ | $84^{ab}$ | $6^b$ | $90^{ab}$ | $6^{ab}$ | $96^a$ |
| 6 | C | 100 | — | $3^c$ | $3^c$ | $29^c$ | $32^d$ | $42^a$ | $74^b$ | $9^b$ | $83^{bc}$ | $12^{ab}$ | $95^{ab}$ |
| 7 | Sep C | 93 | $1^b$ | $2^c$ | $3^c$ | $16^c$ | $19^d$ | $19^b$ | $38^c$ | $28^a$ | $66^c$ | $17^a$ | $83^b$ |

Values with different superscripts differ significantly, P < 0.05

TABLE 11

FECUNDITY AND MEAN CONCEPTION DATES IN MATURE BORDER ROMNEY EWES WHICH RECEIVED VARIOUS COATED IMPLANT TREATMENTS PRIOR TO JOINING ON 28 JANUARY.

| GROUP | NUMBER SCANNED | 0 | SINGLE | TWIN | TRIP | FETUSES/100 EWE IN GROUP | REL. TO GR.7. | MEAN CONC. DATE (1985) | DAYS AFTER JOINING |
|---|---|---|---|---|---|---|---|---|---|
| 1 | 99 | 9 | 81 | 9 | 0 | 100.0$^d$ | 0.877 | 52 | 24 |
| 2 | 104 | 6 | 65 | 33 | 0 | 126.0$^{abc}$ | 1.105 | 50 | 22 |
| 3 | 98 | 4 | 72 | 22 | 0 | 118.4$^{bc}$ | 1.039 | 54 | 26 |
| 4 | 120 | 6 | 51 | 45 | 0 | 138.2$^a$ | 1.212 | 56 | 28 |
| 5 | 98 | 2 | 65 | 31 | 0 | 129.6$^{abx}$ | 1.137 | 58 | 30 |
| 6 | 100 | 5 | 75 | 20 | 0 | 114.0$^{bcd}$ | 1.000 | 61 | 33 |
| 7 | 93 | 10 | 60 | 23 | 0 | 114.0$^{cd}$ | 1.000 | 65 | 37 |

$^{a,b,c,d}$Values with different superscripts differ significantly, P 0.05
$^x$Indicates group 5 is significantly different to group 4.

TABLE 12

EFFECT OF IMPLANT TREATMENT ON FERTILITY AND FECUNDITY OF BLxM EWES JOINED AT VARIOUS TIMES OF THE YEAR

| Group/ joining time | T | Pregnancy Diagnosis Not preg. | Single | Twin | Triplet | Fetuses/ 100 ewes | Absol. change fetuses/ 100 ewes | Relative change as % of control. |
|---|---|---|---|---|---|---|---|---|
| A 30/9/85 | C | 18 | 70 | 14 | — | 96.1 | — | |
|  |  |  |  |  |  | ** | +19.64 | +20.39 |
|  | T | 17 | 52 | 33 | — | 115.7 | — | |
| B 11/11/85 | C | 6 | 84 | 12 | — | 105.9 | | |
|  |  |  |  |  |  | *** | +26.1 | +25.62% |
|  | T | 5 | 59 | 39 | — | 133.0 | | |
| C 23/12/85 | C | 17 | 66 | 18 | — | 101.0 | — | |
|  |  |  |  |  |  | *** | +26.2 | +26.34% |
|  | T | 12 | 53 | 36 | 2 | 127.2 | | |
| D 3/2/86 | C | 18 | 46 | 36 | 2 | 121.6 | — | |
|  |  |  |  |  |  | n.s. | +16.7 | +13.7% |
|  | T | 13 | 39 | 48 | 2 | 138.2 | | |
| E 17/3/86 | C | 8 | 42 | 52 | — | 143 | | |
|  |  |  |  |  |  | n.s. | −8.0 | −5.7 |
|  | T | 12 | 45 | 46 | — | 135 | | |

T: implant administered at 6 and 2 weeks prior to joining.
C: control
n.s. not significant
** = significant at $P < 0.01$
*** = significant at $P < 0.001$

Example 11

Field Trial 5

Comparison of effectiveness of a single implant treatment in ewes of different ages In this trial Merino ewes were given a single coated implant of the kind described in Example 1, at four weeks prior to the introduction of rams. Responses in ewes of two different age groups were tested, the first group being mature parous ewes and the second group being well grown maiden ewes. Control groups consisted of equivalent ewes of the same age groups which did not receive treatment, but which were joined to rams at the same time as the treated animals.

This trial was conducted at Walpeup, Victoria, Australia, and the flocks of ewes were joined to rams on November 14.

RESULTS

Field Trial 5

The treatment enhanced for both mature and maiden animals, the proportion of ewes mating in the first two weeks following introduction of the rams, and in the case of maiden ewes, substantially increased the proportion of ewes mating and conceiving (FIG. 17 and Table 13). The treatment also increased the fecundity of the flock as a whole (i.e. lambs expected/ewe in group) and on an individual ewe basis (i.e. lambs expected/ewe pregnant), this effect being particularly great in the maiden ewes (FIG. 17 and Table 13). The treatment also reduced the number of non-pregnant ewes and resulted in an earlier mean time from introduction of the rams to conception (Table 13).

TABLE 13

EFFECT OF ADMINISTRATION OF A COATED IMPLANT AT 4 WEEKS PRIOR TO JOINING ON THE REPRODUCTIVE PERFORMANCE OF EWES OF DIFFERENT AGE (TRIAL CONDUCTED AT WALPEUP, VICTORIA IN MERINO EWES JOINED TO DORSET RAMS ON NOVEMBER 14.

| Group | Number Scanned | Number Bearing fetuses non preg | sgl | twin | Fetuses/ ewe in group | Fetuses/ per ewe pregnant | Mean mating day | Mean conception day |
|---|---|---|---|---|---|---|---|---|
| 1 Control untreated mature ewes | 121 | 26 | 71 | 24 | 0.98$^a$ | 1.25$^a$ | 18.5 | 21.7 |

TABLE 13-continued

EFFECT OF ADMINISTRATION OF A COATED IMPLANT AT 4 WEEKS PRIOR TO JOINING ON THE REPRODUCTIVE PERFORMANCE OF EWES OF DIFFERENT AGE (TRIAL CONDUCTED AT WALPEUP, VICTORIA IN MERINO EWES JOINED TO DORSET RAMS ON NOVEMBER 14.

| Group | Number Scanned | Number Bearing fetuses | | | Fetuses/ ewe in group | Fetuses/ per ewe pregnant | Mean mating day | Mean conception day |
|---|---|---|---|---|---|---|---|---|
| | | non preg | sgl | twin | | | | |
| 2. Treated mature ewes | 132 | 17 | 61 | 54 | $1.47^b$ | $1.28^b$ | 15.8 | 17.9 |
| 3 Control maiden ewes | 42 | 30 | 11 | 1 | $0.31^c$ | $1.08^c$ | 23.3 | 28.0 |
| 4 Treated maiden ewes | 30 | 9 | 15 | 6 | $0.90^a$ | $1.29^{ab}$ | 14.3 | 18.7 |

$a,b,c$Values with different superscripts differ significantly P 0.05

Example 12

TABLE 14

EFFECT OF COATED IMPLANTS ADMINISTERED IN WINTER (NEAR THE END OF THE NORMAL BREEDING SEASON) IN CORRIEDALE EWES (AT A LATITUDE OF 30° SOUTH)

Treated ewes n = 42 received an implant of the type described in Example 1 on June 12
Control ewes n = 47 were untreated.

| (a) Proportion Ovulating (determined by endoscopy on the dates shown) | | | | | | | | | | |
|---|---|---|---|---|---|---|---|---|---|---|
| | Jul 2 | Jul 23 | Aug 21 | Sep 7 | Oct 16 | Nov 28 | Dec 17 | Jan 7 | Jan 29 | Feb 20 |
| Implanted | 92.85% | 100% | 86.1% | 50% | 18.6% | 0 | 0 | 2.3% | 39.0 | 58.5 |
| Control untreated | 100% | 100% | 82.6% | 30.2% | 8.8% | 0 | 0 | 0 | 50.0 | 79.5 |

| (b) Ovulation Rate/ewe Ovulating | | | | | | | | | | |
|---|---|---|---|---|---|---|---|---|---|---|
| | Jul 2 | Jul 23 | Aug 21 | Sep 7 | Oct 16 | Nov 28 | Dec 17 | Jan 7 | Jan 29 | Feb 20 |
| Implanted | 1.46 | 1.55 | 1.51 | 1.33 | 1.25 | 0 | 0 | 1.00 | 1.19 | 1.21 |
| Control | 1.45 | 1.36 | 1.32 | 1.00 | 1.00 | 0 | 0 | 0 | 1.13 | 1.34 |

| (c) Ovulations/ewe in group | | | | | | | | | | |
|---|---|---|---|---|---|---|---|---|---|---|
| | Jul 2 | Jul 23 | Aug 21 | Sep 7 | Oct 16 | Nov 28 | Dec 17 | Jan 7 | Jan 29 | Feb 20 |
| Implanted | 1.35 | 1.55 | 1.30 | 0.67 | 0.23 | 0 | 0 | 0.02 | 0.46 | 0.71 |
| Control | 1.46 | 1.36 | 1.09 | 0.30 | 0.09 | 0 | 0 | 0 | 0.57 | 1.07 |

Field Trial 6

Effects of coated implant treatment administered at the end of the normal breeding season In this trial, conducted at Werribee, Victoria, Australia, ewes of the Corriedale breed were given a single implant of the type described in Example 1 on June 12, which is towards the end of the natural breeding period for ewes at this latitude. The treated ewes were maintained in isolation from equivalent control ewes, and both groups were maintained in the presence of vasectomized rams throughout the trial period. Oestrus was observed daily and ovarian activity was assessed by laproscopic observation at intervals to 3-5 weeks.

RESULTS

Field Trial 6

Administration of the coated implants late in the season resulted in a prolongation of the breeding season observed as a delay in the normal decline of oestrus activity and ovulation rates in the treated, compated to control ewes (Table 14).

This was particularly evident in August, September and October, following treatment (Table 14).

The delay in cessation of the breeding season was followed by a delay in the commencement of the following breeding season, as shown by the lower proportion of treated ewes ovulating and lower ovulation rate/ewe ovulating in the February following treatment (Table 14).

Example 13

Field Trial 7

Effect of implants on the induction of early breeding in goats

In this trial, conducted at Boort in Victoria, Australia, the effect of administration of a single coated implant of the type described in Example 1 on the onset of oestrus in Angora goats was assessed.

An implant was administered at four weeks prior to joining to each doe in two separate groups, which were maintained in isolation from each other and which were exposed to fertile bucks on December 16. Three separate groups of control (untreated) does were exposed to bucks at the same time. Occurrence of oestrus (assessed by mating marks) was observed at intervals of 4-16 days, commencing ten days after introduction of the bucks.

RESULTS

Field Trial 7

Treatment with the coated implant induced significantly more does in each of the treated groups compared with the control groups to mate during the first few weeks after introduction of the bucks and slightly enhanced the proportion of does mating during the joining period (Table 15).

TABLE 15

EFFECT OF ADMINISTRATION OF INPLANTS TO MATURE ANGORA DOES AT 4 WEEKS PRIOR TO THE INTRODUCTION OF FERTILE BUCKS (DAY 0 OF TRIAL) ON THE NUMBER OF DOES EXPRESSING OESTRUS AT VARIOUS TIMES AFTER JOINING ON DECEMBER 16

| GROUP | SIRE* GROUP | n | 26/12 10 DAYS | 30/12 14 DAYS | 5/1 20 DAYS | 13/1 28 DAYS | 25/1 40 DAYS | 29/1 44 DAYS | 14/2 60 DAYS | TOTAL MATINGS |
|---|---|---|---|---|---|---|---|---|---|---|
| TREATMENT | 1 | 35 | 1 | 2 | 7 | 17 | 2 | | 1 | 30 |
| | 2 | 35 | | | 4 | 29 | | | | 33 |
| TOTAL | | 70 | 1 | 2 | 11 | 46 | 2 | 0 | 1 | 63 |
| CUMULATIVE % | | | 1.4 | 4.3 | 20.0 | 85.7 | 88.6 | 88.6 | 90.0 | 90.0 |
| CONTROL | 3 | 35 | | | 3 | 9 | 19 | | | 31 |
| | 4 | 35 | | | | 6 | 24 | 1 | 1 | 32 |
| | 5 | 35 | | | | 2 | 14 | 11 | | 27 |
| TOTAL | | 105 | 0 | 0 | 3 | 17 | 57 | 12 | 1 | 90 |
| CUMULATIVE % | | | 0 | 0 | 2.0 | 19.0 | 73.3 | 84.8 | 85.7 | 85.7 |

*Groups of 35 treated or control does were mated to separate sires.

Example 14

Field Trials 8 & 9

Effect of implants on the induction of early breeding and pelage changes in deer hinds The first study (Field Trial 8) in this example was conducted near Canterbury in New Zealand, and was to assess the effect of coated implants on the induction of an early breeding season and pellage changes in mature red deer hinds.

Eight mature red deer hinds (Group 1) were each given two implants, of the type described in Example 1, on December 20 and again on January 20. Thus, a total of four implants were given to each hind. A second group of eight similar hinds were given a similar sequential treatment, except that the first two implants were given on January 20 and the second implants on February 18. A third group of eight similar hinds were kept as control (untreated) animals.

Changes in pellage were noted regularly and the proportion of hinds which had ovulated by March 18 was determined by endoscopic examination of the ovaries and by analysis of plasma progesterone levels.

The second study (Field Trial 9) of red deer hinds was conducted near Invermay in New Zealand to assess the effect of implants, made according to Example 1, on the reproductive performance of maiden red deer hinds.

16 hinds were each given two coated implants on December 18 and then subsequently the treatments were repeated at 28 day intervals in January and February. Six untreated maiden hinds were maintained as control. Ovulation was synchronized by either intravaginal progesterone pessaries inserted on February 17 and removed on March 4 (Groups 1 and 3) or by two prostaglandin F2 injections (250u cloprosterol, Estrumate, ICI) on February 21 and March 3 (Group 2). Evidence of ovulation was determined by laparoscopic observation of the ovaries of all hinds on March 12.

RESULTS

First Study, Field Trial 8

The implant treatments commencing on either December 20 or January 20 resulted in an earlier moulting of the summer coat (Table 16) and an earlier onset to ovarian activity in the hinds (Table 17). The extent to which the moult and ovarian activity was brought forward by treatment was positively correlated to the time of commencement of treatment (i.e. the earlier the treatment, the earlier the response). Analysis of progesterone levels in the plasma collected weekly from all hinds confirmed that pregnancy was induced earlier in the treated hinds than in control hinds following introduction of fertile stags to all groups on January 19.

RESULTS

Second Study, Field Trial 9

Treatment of maiden hinds induced an earlier onset to the seasonal pattern of ovarian activity as judged by the increased proportion of hinds observed to have a functional corpus luteum at endoscopy (Table 18). Since the prostaglandin treatment provided an effective synchronization, it is possible that the treated hinds had commenced ovarian cyclicity prior to the synchronization treatment (i.e. prior to February 21).

TABLE 16

INDUCTION OF EARLY MOULT IN RED DEER HINDS BY ADMINISTRATION OF MELATONIN IMPLANTS

| | | | | CUMULATIVE NUMBER (%) OF HINDS IN WHICH SUMMER MOULT WAS OBSERVED | | |
|---|---|---|---|---|---|---|
| GROUP | TREATMENT SCHEDULE | | n | MAR 3 | MAR 18 | MAR 24 |
| 1 | 2 implants DEC 20 + JAN 20 | | 8 | 6 (75%) | 8 (100%) | 8 (100%) |
| 2 | 2 implants JAN 20 + FEB 18 | | 8 | 0 | 7 (87.5%) | 8 (100%) |
| 3 | Control - untreated | | 8 | 0 | 0 | 3 (37.5%) |

TABLE 17
OCCURRENCE OF OVULATION FOLLOWING TREATMENT OF RED DEER HINDS WITH MELATONIN IMPLANTS

| GROUP | TREATMENT SCHEDULE | n | NUMBER (%) OF HINDS OVULATED ON MARCH 18 |
|---|---|---|---|
| 1 | 2 implants DEC 20 + JAN 20 | 8 | 7 |
| 2 | 2 implants JAN 20 + FEB 18 | 8 | 4 |
| 3 | Control - untreated | 8 | 0 |

TABLE 18
EFFECT OF MELATONIN IMPLANTS ADMINISTERED ON DECEMBER 10, AND THEREAFTER AT 28 DAY INTERVALS (2 IMPLANTS/DOSE) ON THE OCCURRENCE OF OVULATION IN MAIDEN RED DEER HINDS.

| GROUP | MELATONIN TREATMENT SCHEDULE | SYNCHRONIZATION SCHEDULE | n | NUMBER (%) OVULATED AT ENDOSCOPY ON MARCH 12 |
|---|---|---|---|---|
| 1 | Implants given at 28 day intervals commencing Dec 10 then in Jan and Feb | Vaginal progestagen pessary Feb 17-Mar 4 | 8 | 7 (87.5%) |
| 2 | Implants given at 28 day intervals commencing Dec 10 then in Jan and Feb | PGF2 250 ug injection Feb 21 & Mar 3 | 8 | 5 (62.5%) |
| 3 | Control - untreated | Vaginal progestagen pessary Feb 17-Mar 4 | 6 | 0 (0%) |

Example 15

Field Trial 10

Effect of implants on the induction of early breeding activity in deer stags

This study, conducted near Invermay in New Zealand, was conducted to assess the effects of coated implants on the timing of changes associated with the run in mature red deer stags.

Four groups of stags were treated, as follows:

Group 1 (n=6) received two doses each of two coated implants of a type described in Example 1. The first dose was administered on November 8, and the second on December 9. Group 2 (n=6) similarly received two doses of two coated implants, the first on December 9 and the second on January 9. Group 3 (n=6) were untreated control stags, grazed together with groups 1 and 2. Group 4 (n=6) were untreated control stags, grazed in isolation from the other treated and control groups.

Monthly observations were made of bodyweight, testes diameter, testes circumference and neck girth to assess the effect of implants on these seasonally variable physiological parameters.

RESULTS

Field Trial 10

Treatment of stags with implants induced an early onset to the seasonal pattern of testis circumference (FIG. 18a), testis diameter (FIG. 18b), liveweight (FIG. 18c) and neck girth (FIG. 18d). The extent to which these parameters were brought forward in time was related to the time of commencement of treatment, with the stags first treated in November showing earlier increases in testis size and correlated androgen dependent changes, such as neck girth, than the December treated stags.

Example 16

Field Trial 11

Effect of implants on the induction of pellage changes in mink

The purpose of this trial, conducted in Wisconsin in the United States of America, was to observe the effect of melatonin implants, prepared as described for Examples 2 and 3, on the occurrence of seasonal changes in pellage of the mink. Three treatment groups were allocated, as follows:

Group 1 received a single implant of the type described in Example 2.

Group 2 received a single implant of the type in Example 3.

Group 3 (untreated, control) received a sham implantation procedure, in which the implanting needle was placed under the skin, but no implant was inserted.

Implants were inserted, or sham implantations performed, on July 13.

Each treatment group included immature kit males and females and mature males and females.

All mink were given a high protein pelling diet from August 1. On August 18, a fourth completely separate group of mature male and female mink (n=67) were also put onto the high protein diet to obtain data on animals managed according to the normal practice of the farm. All animals were observed frequently for pelt condition and most were pelted at a time when the pelt was judged to be at optimum condition.

RESULTS

Field Trial 11

Treatment with either implants resulted in the formation of the winter pelt in both mature and immature males and females at a time much earlier than that observed in the control groups (Table 9). Treated male mink appeared to reach prime about three days later than treated females, but both were significantly ahead of untreated animals put onto the high protein diet at the same time (Group 13) or the untreated put onto the pelting diet at the normal time of August 18 (Group 4).

TABLE 19

EFFECT OF MELATONIN IMPLANTS ADMINISTERED ON JULY 13 ON THE OCCURRENCE OF WINTER PELTS IN IMMATURE AND MATURE MALE AND FEMALE MINK

| GROUP | AGE | SEX | n TOTAL | MELATONIN DOSE | PELT DATE | DIET | DEATHS OBSVD. | OCCURRENCE OF PRIME ||||
|---|---|---|---|---|---|---|---|---|---|---|---|
| | | | | | | | | SEP 15 | OCT 6 | OCT 9 | DEC 15 |
| 1 | MATURE | M | | | | | 1 | | | | |
| | | F | 34 | 20 mg | JUL 13 | AUG 1 | — | 0 | | | |
| | KIT | M | | | | | — | | | | |
| | | F | | | | | — | | 39/40F | | 1/40F |
| | | | | | | | | | | 26/26M | |
| 2 | MATURE | M | | | | | 1 | | | | |
| | | F | 34 | 10 mg | JUL 13 | AUG 1 | — | 0 | | | |
| | KIT | M | | | | | — | | | | |
| | | F | | | | | — | | | | |
| 3 | MATURE | M | | | | | 1 | | | | |
| | | F | 34 | 0 mg Sham | JUL 13 | AUG 1 | 4 | 0 | 0 | 0 | 34/34 |
| | KIT | M | | | | | — | | | | |
| | | F | | | | | — | | | | |
| 4 | MATURE | M | 67 | 0 mg | — | AUG 18 | — | 0 | 0 | 0 | 67/67 |
| | | F | | | | | | | | | |

We claim:

1. A coated veterinary implant comprising:
(a) a veterinary implant including an effective amount of:
 (i) an active ingredient selected from the group consisting of melatonin, melatonin analogues, and mixtures thereof, wherein said melatonin analogues and mixtures thereof exert substantially the same biological effect on seasonal breeding activity or other seasonal physiological responses of animals as said melatonin; and
(b) a coating for said veterinary implant (a) formed from a physiologically compatible polymeric coating composition comprising a water-insoluble film-forming high molecular weight polymer; which implant, in use, releases said active ingredient at a rate sufficient to maintain the blood level of said active ingredient at or above a level sufficient, and for a period sufficient, to regulate seasonal breeding activity or other seasonal physiological responses of an animal to be treated.

2. The coated veterinary implant of claim 1 wherein said active ingredient is melatonin.

3. The coated veterinary implant of claim 1 wherein said active ingredient is selected from the group consisting of seratonin, N,O-diacetylserotonin, 5-methoxytryptophol, and 5-methoxytryptamine.

4. The coated veterinary implant of claim 1 wherein said active ingredient is selected from the group consisting of tryptamine, 5-methoxytryptamine, serotonin, 6-chloro-(2,3-dihydro)melatonin, 2,3-dihydromelatonin, and 5-hydroxykynurenine wherein the 5-hydroxy is unsubstituted or is substituted with methyl, ethyl or propyl; and wherein said active ingredient comprises an amino substituent selected from the group consisting of N-alkyl, N,N-dialkyl, N-aryl, N,N-diaryl, N-alkyl(aryl), ureido, acetyl, propionyl, and butyrl.

5. The coated veterinary implant of claim 1 wherein said active ingredient is selected from the group consisting of melatonin, 2,3-dihydromelatonin, N-propionyl melatonin, N-butyrylmelatonin, N-acetylserotonin, N-O-diacetylserotonin, N-acetyltryptamine, serotonin, 5-methoxytryptophol and 5-methoxytryptamine; wherein said active ingredient comprises a 6-substituent selected from the group consisting of halo, hydroxy, sulfatoxy, alkyl, alkoxy and siloxy.

6. The coated veterinary implant of claim 1 wherein said active ingredient is selected from the group consisting of N-acetyltryptamine, tryptamine, 2,3-dihydromelatonin, 6-chloro-(2,3-dihydro)melatonin, and N-acetylserotonin; wherein said active ingredient comprises a 5-substituent selected from the group consisting of ethoxy and propoxy.

7. The coated veterinary implant of claim 1 wherein said active ingredient, in use, is released at a rate sufficient to maintain the blood level of said active ingredient at or above about 1000 picomolar for at least about three weeks.

8. The coated veterinary implant of claim 1 wherein said active ingredient is present in an amount of about 75–98% by weight based on the total weight of said coated implant.

9. The coated veterinary implant of claim 1 wherein said water-insoluble film-forming high molecular weight polymer is selected from the group consisting of cellulose polymers, acrylic polymers, and mixtures thereof.

10. The coated veterinary implant of claim 1 wherein said active ingredient is present in an amount of from about 25–75% by weight based on the total weight of the coated implant.

11. The coated veterinary implant of claim 1 wherein said veterinarily acceptable carrier or excipient comprises:
(a) about 1–70% by weight of a compressible pharmaceutical vehicle;
(b) about 1–10% by weight of a granulating agent; and
(c) about 0.1–5% by weight of a compression lubricant.

12. A coated veterinary implant comprising:
(a) a veterinary implant comprising about 2.5–100 mg of melatonin, about 2.5–5.0 mg of ethyl cellulose, and about 0.2–0.3 mg of a compression lubricant; and
(b) a first coating for said veterinary implant comprising about 0.01–1.0 mg of ethyl cellulose polymer.

13. The coated veterinary implant of claim 12 wherein said veterinary implant (a) further comprises an effective amount of up to about 0.2 mg polyvinylpyrrolidone.

14. The coated veterinary implant of claim 13 further comprising:
(c) a second coating for said veterinary implant comprising about 0.01-1.0 mg of ethyl cellulose polymer.

15. The coated veterinary implant of claim 1 of generally cylindrical shape and having a length of about 3-10 mm and a diameter of about 2-3 mm.

16. A method of regulating the seasonal breeding activity or other seasonal physiological responses of animals, said method comprising inserting into an animal to be treated at a suitable implantation site at least one coated veterinary implant of claim 1.

17. The method of claim 16 wherein at least two coated veterinary implants are inserted.

18. The method of claim 16 wherein the implantation site is a subcutaneous implantation site.

19. The method of claim 16 wherein the animal is a prepubescent animal and the seasonal breeding activity is regulated by delaying the onset of puberty.

20. The method of claim 16 wherein the animal is a female animal and the seasonal breeding activity is regulated by advancing the onset of oestrus.

21. The method of claim 16 wherein the seasonal breeding activity is regulated by extending the seasonal breeding activity, and wherein the coated veterinary implant is inserted after the normal breeding cycle has commenced.

22. The method of claim 16 wherein the coated veterinary implant generates a second peak in seasonal breeding activity.

* * * * *

UNITED STATES PATENT AND TRADEMARK OFFICE
CERTIFICATE OF CORRECTION

PATENT NO. : 4,882,137

DATED : November 21, 1989

INVENTOR(S) : L. D. Staples, et al.

It is certified that error appears in the above-identified patent and that said Letters Patent is hereby corrected as shown below:

At col. 4, line 4, "iacetyl" should read --diacetyl--.

At col. 14, line 23, "ostrus" should read --oestrus--.

At col. 17, line 67, "conceptio" should read --conception--.

At col. 18, line 33, "Sorino" should read --Spring--.

At col. 21, line 55, after "such" should be inserted --that--.

At col. 23, line 10, after "such" should be inserted --that--.

At col. 25, Table 11 in footnotes a, b, c, d, "P 0.05" should read --P<0.05--.

At col. 27, Table 13 in footnotes a, b, c, "P 0.05" should read --P<0.05--.

At col. 33, line 59, "butyrl" should read --butyryl--.

Signed and Sealed this

Twenty-fourth Day of July, 1990

*Attest:*

HARRY F. MANBECK, JR.

*Attesting Officer*     *Commissioner of Patents and Trademarks*